(12) United States Patent
Yang et al.

(10) Patent No.: US 8,729,277 B2
(45) Date of Patent: May 20, 2014

(54) PROCESSES FOR THE SYNTHESIS OF GAMMA NITROCARBONYL AND GAMMA DICARBONYL COMPOUNDS AND THEIR PYRROLE DERIVATIVES

(75) Inventors: Hu Yang, Manvel, TX (US); Eduardo J. Baralt, Kingwood, TX (US)

(73) Assignee: Chevron Philips Chemical Company LP, The Woodlands, TX (US)

( * ) Notice: Subject to any disclaimer, the term of this patent is extended or adjusted under 35 U.S.C. 154(b) by 100 days.

(21) Appl. No.: 13/406,677

(22) Filed: Feb. 28, 2012

(65) Prior Publication Data

US 2012/0157692 A1 Jun. 21, 2012

Related U.S. Application Data

(62) Division of application No. 12/418,661, filed on Apr. 6, 2009, now Pat. No. 8,148,545.

(51) Int. Cl.
*C07C 45/40* (2006.01)
*C07D 207/323* (2006.01)

(52) U.S. Cl.
USPC .......... 548/564; 568/307; 568/383; 568/412; 568/943

(58) Field of Classification Search
USPC .......................................... 568/383, 412, 943
See application file for complete search history.

(56) References Cited

U.S. PATENT DOCUMENTS 6,229,051 B1 * 5/2001 Sandefur .................. 568/351
8,148,545 B2 * 4/2012 Yang et al. ................ 548/400
2010/0256391 A1 10/2010 Yang et al.

OTHER PUBLICATIONS

Ballini et al J. Org. Chem. (2003), vol. 68, p. 9173-9176.*
Ballini, et al., J. Org. Chem., 68, 9173-9176, 2003.
Ballini, et al., Tetrahedron Letter, 37:44, 8027-8030, 1996.
Setter, et al., Org. Syn., Coll., vol. 8, p. 620, 1993.
Shaabani, et al., Tetrahedron Letter, 42:34, 5833-5836, 2001.
Yasuda, et al., J. Org. Chem, 62, 8282-8283, 1997.
Young, et al., Org. Syn., Coll., vol. 2, p. 219, 1943.

* cited by examiner

*Primary Examiner* — Yong Chu
(74) *Attorney, Agent, or Firm* — Merchant & Gould

(57) ABSTRACT

The present invention discloses processes for producing γ-nitrocarbonyl and γ-dicarbonyl compounds, which can be precursors in the synthesis of pyrrole compounds. A process for producing pyrroles such as 2,5-dimethylpyrrole, and structurally similar pyrrole compounds, is also disclosed.

32 Claims, 4 Drawing Sheets

PROCESSES FOR THE SYNTHESIS OF GAMMA NITROCARBONYL AND GAMMA DICARBONYL COMPOUNDS AND THEIR PYRROLE DERIVATIVES

REFERENCE TO RELATED APPLICATION

This application is a divisional application of U.S. patent application Ser. No. 12/418,661, filed on Apr. 6, 2009, now U.S. Pat. No. 8,148,545, which is incorporated herein by reference in its entirety.

BACKGROUND OF THE INVENTION

The present invention relates generally to processes for producing γ-nitrocarbonyl compounds, γ-dicarbonyl compounds, and pyrrole compounds.

The γ-nitrocarbonyl and γ-dicarbonyl compounds can be precursors that are employed in the synthesis of pyrrole compounds. Certain pyrrole compounds—for example, 2,5-dimethylpyrrole—can be used as a component in an oligomerization catalyst system to produce an α-olefin oligomer, such as 1-hexene or 1-octene, from ethylene.

SUMMARY OF THE INVENTION

Methods of synthesizing a variety of organic compounds containing one or more carbonyl groups are disclosed herein. In accordance with one aspect of the present invention, a process for producing a γ-nitrocarbonyl compound is provided. This process comprises:

a) contacting a primary or secondary nitro compound, an α,β-unsaturated carbonyl compound, a base, and water; and b) forming the γ-nitrocarbonyl compound in a yield of at least about 75 mole %.

Processes for producing γ-dicarbonyl compounds also are provided in the present invention. One such process comprises:

a) contacting a γ-nitrocarbonyl compound, a peroxide compound, a base, and water, wherein a molar ratio of the peroxide compound to the γ-nitrocarbonyl compound is in a range from about 1:1 to about 15:1; and b) forming the γ-dicarbonyl compound.

Another process for producing a γ-dicarbonyl compound is disclosed and, in this process, the starting materials are an α,β-unsaturated carbonyl compound and a primary nitro compound. This process comprises:

a) contacting a primary nitro compound, an α,β-unsaturated carbonyl compound, a base, and water to produce a γ-nitrocarbonyl compound; and b) contacting a peroxide compound with the γ-nitrocarbonyl compound at a molar ratio of the peroxide compound to the γ-nitrocarbonyl compound in a range from about 1:1 to about 15:1 to produce the γ-dicarbonyl compound.

The γ-nitrocarbonyl and γ-dicarbonyl compounds produced in accordance with this invention can be used to synthesize pyrrole compounds. For instance, a process for producing a pyrrole compound can comprise the following steps:

a) contacting a γ-nitrocarbonyl compound, a peroxide compound, a base, and water, wherein a molar ratio of the peroxide compound to the γ-nitrocarbonyl compound is in a range from about 1:1 to about 15:1;

b) forming a γ-dicarbonyl compound; and c) contacting the γ-dicarbonyl compound with ammonia or an ammonium salt to produce the pyrrole compound.

DEFINITIONS

Figure 1:
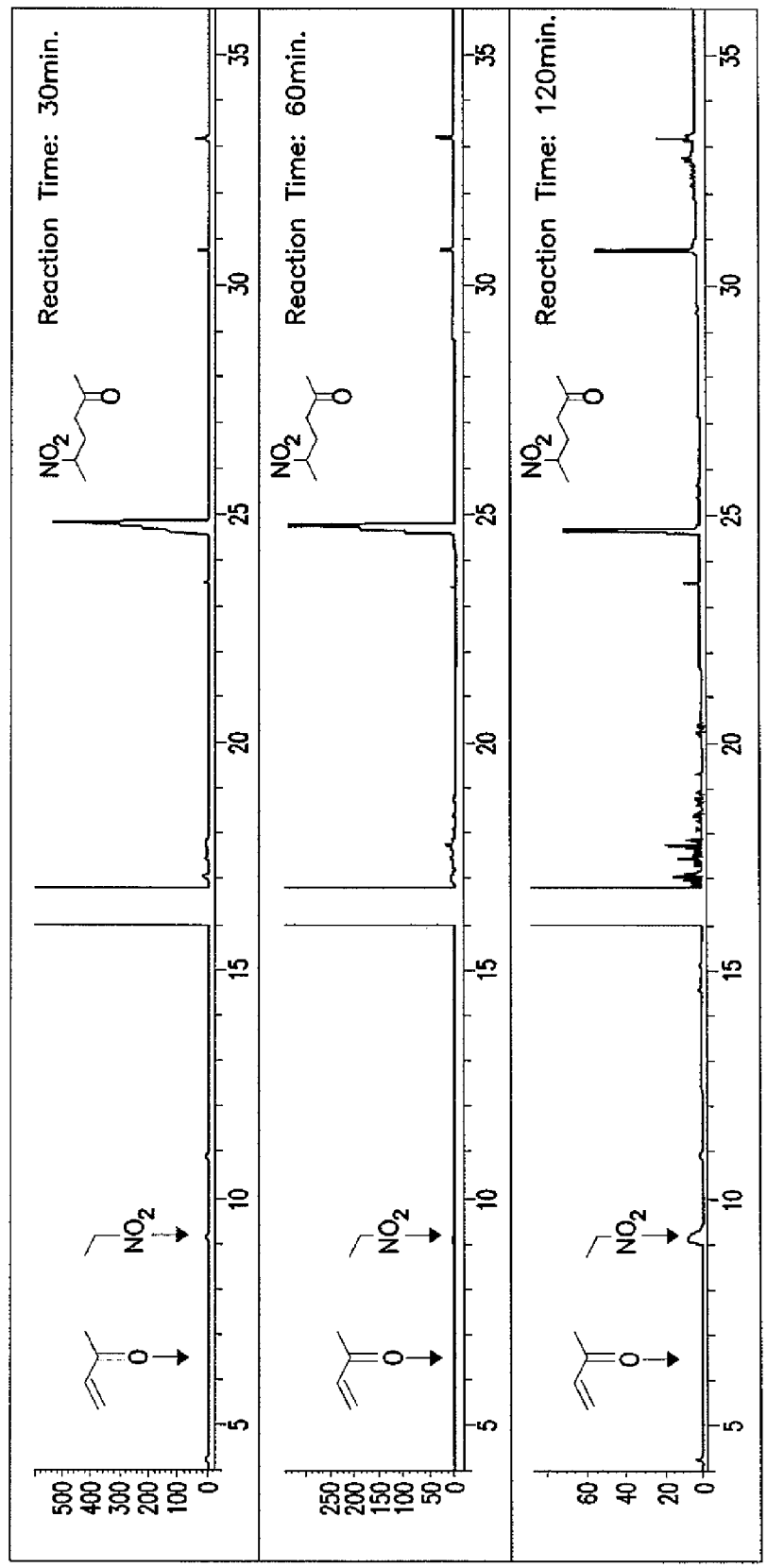
FIG. 1 presents Gas Chromatograph plots of the reaction mixture of Example 2 at reaction times of 30 minutes, 1 hour, and 2 hours.

To define more clearly the terms used herein, the following definitions are provided. To the extent that any definition or usage provided by any document incorporated herein by reference conflicts with the definition or usage provided herein, the definition or usage provided herein controls.

As used herein, the term "α,β-unsaturated carbonyl compound" and its derivatives refer to aldehyde(s) or ketone(s) having a carbon atom of a carbon-carbon double bond attached to the carbonyl carbon atom (the carbon atom bearing the double bonded oxygen atom of the aldehyde or ketone group). Similarly, the term "α,β-unsaturated aldehyde" and its derivatives refer to compounds having a carbon atom of a carbon-carbon double bond attached to the carbonyl carbon atom (the carbon atom bearing the double bonded oxygen atom of the aldehyde carbonyl group). Likewise, the term "α,β-unsaturated ketone" and its derivatives refer to compounds having a carbon atom of a carbon-carbon double bond attached to the carbonyl carbon atom (the carbon atom bearing the double bonded oxygen atom of the ketone carbonyl group). While the α,β-unsaturated carbonyl compound, α,β-unsaturated aldehyde, and α,β-unsaturated ketone must minimally contain at least the two groups having the designated relationship, the compounds may contain additional carbon-carbon double bonds, aldehyde groups, and/or ketone groups, which may or may not have the designated relationship. Additionally, unless otherwise specified, the α,β-unsaturated carbonyl compound, the α,β-unsaturated aldehyde compound, and the α,β-unsaturated ketone compound may contain other functional groups and/or heteroatoms.

In this disclosure, the term "γ-nitrocarbonyl compound" and it derivatives refer to aldehyde(s) or ketone(s) having a nitro group attached to the third carbon atom from the carbonyl carbon atom (the carbon atom bearing the double bonded oxygen atom of the aldehyde or ketone group). In this application, the term "γ-nitroaldehyde compound" and its derivatives refer to compounds having a nitro group attached to the third carbon atom from the carbonyl carbon atom (the carbon atom bearing the double bonded oxygen atom of the aldehyde group). Also, in this application, the term "γ-nitroketone compound" and its derivatives refer to compounds having a nitro group attached to the third carbon atom from the carbonyl carbon atom (the carbon atom bearing the double bonded oxygen atom of the ketone group). While the γ-nitrocarbonyl compound, γ-nitroaldehyde compound, and γ-nitroketone must minimally contain at least the two groups having the designated relationship, the compounds may contain additional nitro groups, aldehyde groups, and/or ketone groups, which may or may not have the designated relationship. Additionally, unless otherwise specified, the γ-nitrocarbonyl compound, γ-nitroaldehyde compound, and γ-nitroketone may contain other functional groups and/or heteroatoms.

In like manner, the term "γ-dicarbonyl compound" and it derivatives refer to compound(s) having two ketone groups, two aldehyde groups, or an aldehyde group and a ketone group, separated by two contiguous carbon atoms. For the purpose of this application, the term "γ-dialdehyde compound" and its derivatives refer to compounds having two aldehyde groups separated by two contiguous carbon atoms. Likewise, for the purpose of this application, the term "γ-aldehyde ketone compound" and its derivatives refer to compounds having an aldehyde and a ketone group separated by two contiguous carbon atoms. Additionally, in this application, the term "γ-diketone compound" and its derivatives refer to compounds having two ketone groups separated by two contiguous carbon atoms. While the γ-dicarbonyl compound, γ-dialdehyde compound, γ-aldehyde ketone compound, and γ-diketone compound must contain at least the two groups in the designated relationship, these compounds may contain additional aldehyde and/or ketone groups, which may or may not have the designated relationship. Additionally, unless otherwise specified, the γ-dicarbonyl compound, γ-dialdehyde compound, γ-aldehyde ketone compound, or γ-diketone compound may contain other functional groups and or heteroatoms.

The term "hydrocarbyl group" is used herein in accordance with the definition specified by IUPAC: a univalent group formed by removing a hydrogen atom from a hydrocarbon (i.e., a group containing only carbon and hydrogen). Similarly, a "hydrocarbylene group" refers to a group formed by removing two hydrogen atoms from a hydrocarbon. A "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be an aliphatic, inclusive of acyclic and cyclic groups, or aromatic. A "hydrocarbyl group," "hydrocarbylene group," and "hydrocarbon group" can include rings, ring systems, aromatic rings, and aromatic ring systems which contain only carbon and hydrogen. Hydrocarbyl groups, hydrocarbylene groups, and hydrocarbon groups include, by way of example, aryl, arylene, alkyl, alkylene, cycloalkyl, cycloalkylene, aralkyl, aralkylene, and combinations of these groups, among others. Hydrocarbyl groups, hydrocarbylene groups, and hydrocarbon groups may be linear or branched unless otherwise specified.

For purposes of this application, an "organyl group" has the definition specified by IUPAC: an organic substituent group, regardless of functional type, having one free valence at a carbon atom. Similarly, an "organylene group" refers to an organic group, regardless of functional type, formed by removing two hydrogen atoms from one or two carbon atoms of an organic compound and an "organic group" refers to a generalized organic group formed by removing one or more hydrogen atoms from one or more carbon atoms of an organic compound. Thus, an "organyl group," an "organylene group," and an "organic group" can contain organic functional group(s) and/or atom(s) other than carbon and hydrogen (i.e., an organic group that can comprise functional groups and/or atoms in addition to carbon and hydrogen). For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. An "organyl group," "organylene group," or "organic group" may be aliphatic, inclusive of acyclic and cyclic groups, or aromatic. Organyl groups, organylene groups, and organic groups also encompass heteroatom-containing rings, heteroatom-containing ring systems, heteroaromatic rings, and heteroaromatic ring systems. Finally, it should be noted that the "organyl group," "organylene group," or "organic group" definitions include the organyl, organylene, or organic group consisting of inert functional groups, respectively, and the hydrocarbyl, hydrocarbylene, and hydrocarbon group, respectively as a members. Organyl groups organylene groups, and organic groups may be linear or branched unless otherwise specified.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which are inert under the process conditions defined herein. Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups. Thus, the terms or variations of the terms "organyl groups consisting of inert functional groups," "organylene group consisting of inert functional groups," and "organic group consisting of inert functional groups" further define the particular organyl groups that can be present within the organyl group, organylene, or organic group consisting of inert functional groups. Additionally, the terms "organyl group consisting of inert functional groups," "organylene group consisting of inert functional groups," and "organic group consisting of inert functional groups" can refer to the presence of one or more inert functional groups within the group. The terms or variations of the terms "organyl group consisting of inert functional groups," "organylene group consisting of inert functional groups," and "organic group consisting of inert functional groups" definition includes hydrocarbyl, hydrocarbylene, and hydrocarbon groups, respectively, as a member. An "organyl group consisting of inert functional groups," "organylene group consisting of inert functional groups," and "organic group consisting of inert functional groups" can be an aliphatic, inclusive of acyclic and cyclic groups, or aromatic groups. An organyl group consisting of inert functional groups, organylene group consisting of inert functional groups, and organic group consisting of inert functional groups may be linear or branched unless otherwise specified.

As used herein, an "inert functional group" is a group which does not substantially interfere with the processes described herein in which the material having an inert functional group takes part. Examples of inert functional groups which do not substantially interfere with the processes described herein include, but are not limited to, halo (fluoro, chloro, bromo and iodo), ethers (alkoxy group or ethyl group), sulfides (sulfidyl group), hydrocarbyl groups, and the like, or combinations of these groups.

The terms "contact product," "contacting," and the like, are used herein to describe compositions wherein the components are contacted together in any order, in any manner, and for any length of time. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

The term "effective concentration" and its derivatives (e.g., "initial effective concentration") are used herein to refer to the total concentration of compound/species capable of forming the reactive compound/species present in the solution. For example, it is known that a base can deprotonate a primary nitro compound to form an anion of the primary nitro compound. Depending on the identity of the base and the quantity of the base, both the primary nitro compound and the anion of the primary nitro compound may be present in the solution. Thus, the "effective concentration" of a primary nitro compound would be the concentration of the primary nitro compound plus the concentration of the anion of the primary nitro compound. Similarly, the "initial effective concentration" of a primary nitro compound would be the initial concentration of the primary nitro compound plus the initial concentration of the anion of the primary nitro compound before either the primary nitro compound or the anion of the primary nitro compound reacts with another compound. Typically, the effective concentration can be determined from knowledge of the amount of materials added to the solution (e.g., the amount of primary nitro compound added to the solution).

The terms "a," "an," and "the" are intended to include plural alternatives, e.g., at least one. For instance, the disclosure of "a base," "a peroxide compound," a "γ-dicarbonyl compound," etc., is meant to encompass one, or mixtures or combinations of more than one, base, peroxide compound, γ-dicarbonyl compound, etc., unless otherwise specified.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any structure presented also encompasses all conformational isomers, regioisomers, and stereoisomers that may arise from a particular set of substituents, unless otherwise specified. The structure also encompasses all enantiomers, diastereomers, and other optical isomers whether in enantiomeric or racemic forms, as well as mixtures of stereoisomers, as would be recognized by a skilled artisan, unless otherwise specified.

Applicants disclose several types of ranges in the present invention. These include, but are not limited to, a range of number of atoms, a range of molar ratios, a range of temperatures, a range of reaction times, a range of yields, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a hydrocarbyl group having from 1 to 18 carbon atoms (i.e., a $C_1$-$C_{18}$ hydrocarbyl group), as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a hydrocarbyl group having 3 to 12 carbon atoms), and also including any combination of ranges between these two numbers (for example, a hydrocarbyl group having 1 to 4 carbon atoms and a hydrocarbyl group having 8 to 12 carbon atoms).

Similarly, another representative example follows for the molar ratio of a peroxide compound to a γ-nitrocarbonyl provided in one aspect of this invention. By a disclosure that the molar ratio of the peroxide compound to the γ-nitrocarbonyl compound is in a range from about 1:1 to about 15:1, Applicants intend to recite that the molar ratio can be selected from about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1. Additionally, the molar ratio can be within any range from about 1:1 to about 15:1 (for example, the molar ratio is in a range from about 1:1 to about 10:1), and this also includes any combination of ranges between about 1:1 and about 15:1. Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

All product yields disclosed in this application are based on the limiting reactant in the respective reaction. For example, the limiting reactant in a process for synthesizing a γ-nitrocarbonyl compound may be an α,β-unsaturated carbonyl compound and, therefore, the yield of the γ-nitrocarbonyl compound would be based on the initial quantity of the α,β-unsaturated carbonyl compound.

While compositions and methods are described in terms of "comprising" various components or steps, the compositions and methods can also "consist essentially of" or "consist of" the various components or steps.

DETAILED DESCRIPTION OF THE INVENTION

The present invention provides a method of making a variety of organic compounds comprising one or more carbonyl groups. The γ-nitrocarbonyl and γ-dicarbonyl compounds produced in accordance with this invention can be used to synthesize pyrrole compounds which, subsequently, can be used as catalyst components in olefin polymerizations. The methods of this invention generally afford higher yields of the desired product than were available heretofore.

Synthesizing γ-Nitrocarbonyl Compounds

A process for producing a γ-nitrocarbonyl compound can comprise (or alternatively, consistent essentially of, or consist of) the following steps:

a) contacting a primary or secondary nitro compound, an α,β-unsaturated carbonyl compound, a base, and water; and b) forming the γ-nitrocarbonyl compound in a yield of at least about 75 mole %.

Generally, the process for synthesizing a γ-nitrocarbonyl compound is conducted under an inert atmosphere (e.g., a nitrogen or argon atmosphere, among other possibilities), although this is not a requirement. The process can be conducted at a variety of reaction temperatures, ranging from about 10° C. to about 80° C., for instance. Often, the process is conducted at a temperature in a range from about 15° C. to about 60° C., from about 15° C. to about 45° C., or from about 20° C. to about 30° C. In some aspects of this invention, the reaction temperature for this process is room temperature which, in this disclosure, is about 25° C.

The appropriate reaction time for the synthesis of a γ-nitrocarbonyl compound can depend greatly upon the reaction temperature and reagent concentrations that are selected. However, Applicants have found, unexpectedly, that reaction times of 3 hours or more can lead to the excessive formation of impurities and other by-products at the expense of the desired γ-nitrocarbonyl compound. Accordingly, in some aspects of this invention, the process to produce a γ-nitrocarbonyl compound should be conducted in a time period ranging from about 1 minute to about 2 hours. For instance, the reaction time to produce the γ-nitrocarbonyl compound may range from 1 minute to about 90 minutes, from about 5 minutes to about 75 minutes, from about 5 minutes to about 60 minutes, from about 5 minutes to about 45 minutes, or from about 5 minutes to about 30 minutes, in other aspects of this invention.

The process for synthesizing a γ-nitrocarbonyl compound produces the γ-nitrocarbonyl compound in a yield of at least about 75 mole %. Typically, the yield of the γ-nitrocarbonyl compound is at least about 80 mole %. In another aspect, the yield of the γ-nitrocarbonyl compound is at least about 85 mole %. Yet, in another aspect, the yield of the γ-nitrocarbonyl compound is at least about 90 mole %. These yields are based on the moles of the limiting reactant, e.g., the moles of the α,β-unsaturated carbonyl compound.

To produce a γ-nitrocarbonyl compound, a primary or secondary nitro compound, an α,β-unsaturated carbonyl compound, a base, and water are contacted. The base employed in this process can be, but is not limited to, an alkali metal carbonate or an alkaline earth metal carbonate. Accordingly, non-limiting examples of suitable bases include lithium carbonate, sodium carbonate, potassium carbonate, magnesium carbonate, calcium carbonate, and the like, or combinations thereof. In some aspects of this invention, the base is an alkali metal carbonate and, in particular, the alkali metal carbonate can be potassium carbonate.

In one aspect of this invention, the primary or secondary nitro compound is a primary nitroalkane having the formula:

(I)

the α,β-unsaturated carbonyl compound has the formula:

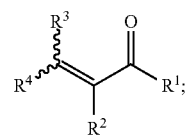

(II)

and the γ-nitrocarbonyl compound has the formula:

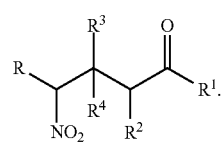

(III)

Formulas (I), (II), and (III) are not designed to show stereochemistry or isomeric positioning of the different moieties (e.g., these formulas are not intended to show cis or trans isomers), although such compounds are contemplated and encompassed by these formulas. R, $R^1$, $R^2$, $R^3$, and $R^4$ independently can be a hydrogen atom, a $C_1$-$C_{30}$ organyl group, a $C_1$-$C_{30}$ organyl group consisting of inert functional groups, or a $C_1$-$C_{30}$ hydrocarbyl group; alternatively, R, $R^1$, $R^2$, $R^3$, and $R^4$ independently can be a hydrogen atom, a $C_1$-$C_{18}$ organyl group, a $C_1$-$C_{18}$ organyl group consisting of inert functional groups, or a $C_1$-$C_{18}$ hydrocarbyl group; or alternatively, R, $R^1$, $R^2$, $R^3$, and $R^4$ independently can be a hydrogen atom, a $C_1$-$C_8$ organyl group, a $C_1$-$C_8$ organyl group consisting of inert functional groups, or a $C_1$-$C_8$ hydrocarbyl group.

In one aspect of the present invention, R and $R^1$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^2$, $R^3$, and $R^4$ are hydrogen. In another aspect, R, $R^1$, and $R^2$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^3$ and $R^4$ are hydrogen; or alternatively, R, $R^1$, and $R^3$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^2$ and $R^4$ are hydrogen. In still another aspect, $R^1$ and $R^3$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and R, $R^2$, and $R^4$ are hydrogen; or alternatively, R and $R^2$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^1$, $R^3$, and $R^4$ are hydrogen. In a further aspect, R, $R^1$, $R^2$, and $R^3$ independently can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^4$ is hydrogen. In yet another aspect, R can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and $R^1$, $R^2$, $R^3$, and $R^4$ are hydrogen; or alternatively, $R^1$ can be a $C_1$-$C_{18}$ organyl group, a $C_1$-$C_{18}$ hydrocarbyl group, a $C_1$-$C_8$ organyl group, or a $C_1$-$C_8$ hydrocarbyl group, and R, $R^2$, $R^3$, and $R^4$ are hydrogen The $C_1$-$C_{18}$ organyl group or $C_1$-$C_8$ organyl group which can be employed as R, $R^1$, $R^2$, $R^3$, and/or $R^4$ can be an acyl group (—C(O)$R^5$), a hydrocarboxycarbonyl group (—CO$_2R^6$), a carbamoyl group (—C(O)NH$_2$), a N-hydrocarbylcarbamoyl group (—C(O)NH$R^7$), or a N,N-dihydrocarbylcarbamoyl group (—C(O)N$R^7R^8$). Alternatively, the $C_1$-$C_{18}$ organyl group or $C_1$-$C_8$ organyl group which can be employed as R, $R^1$, $R^2$, $R^3$, and/or $R^4$ can have the structure —$(CH_2)_n$—Y, wherein Y can be a halide, an alkoxy group (—$OR^9$), a sulfidyl group (—$SR^{10}$), an aminyl group (—$NR^{11}R^{12}$), or a phosphinyl group (—$PR^{13}R^{14}$), and n is a positive integer ranging from 1 to 6. In other embodiments, n of the $C_1$-$C_{18}$ organyl group or $C_1$-$C_8$ organyl group having the structure —$(CH_2)_n$—Y can be a positive integer ranging from 1 to 4; or alternatively, a positive integer ranging from 1 to 3. Alternatively, n of the $C_1$-$C_{18}$ organyl group or $C_1$-$C_8$ organyl group having the structure —$(CH_2)_n$—Y can be 1; alternatively, 2; or alternatively, 3. Within the acyl, hydrocarboxycarbonyl group, N-hydrocarbylcarbamoyl group, N,N-dihydrocarbylcarbamoyl group, and organyl group having the structure —$(CH_2)_n$—Y, $R^5$, $R^6$, $R^7$, $R^8$, $R^9$, $R^{10}$, $R^{11}$, $R^{12}$, $R^{13}$, and $R^{14}$ may be any $C_1$ to $C_{18}$ hydrocarbyl group or $C_1$ to $C_8$ hydrocarbyl group described herein.

The $C_1$-$C_{18}$ hydrocarbyl group or $C_1$-$C_8$ hydrocarbyl group employed as R, $R^1$, $R^2$, $R^3$, and/or $R^4$, or as $R^5$, $R^6$, $R^7$, $R^8$, $R^9$, $R^{10}$, $R^{11}$, $R^{12}$, $R^{13}$, and $R^{14}$ within the acyl, hydrocarboxycarbonyl group, N-hydrocarbylcarbamoyl group, N,N-dihydrocarbylcarbamoyl group, and organyl group having the structure —$(CH_2)_n$—Y, can be an alkyl group, an aryl group, or an alkylaryl group described herein. Alkyl groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl. Aryl and arylalkyl groups include, but are not limited to, phenyl, alkyl-substituted phenyl, naphthyl, alkyl-substituted naphthyl, phenyl-substituted alkyl, naphthyl-substituted alkyl, and the like.

Unless otherwise specified, the disclosure of an alkyl group is intended to include all structural isomers, linear or branched, of a given moiety. Additionally, unless otherwise specified, the disclosure of an alkyl group is intended to include all enantiomers and all diastereomers. As examples, unless otherwise specified, the term propyl is meant to include n-propyl and iso-propyl, the term butyl is meant to include n-butyl, iso-butyl, t-butyl, sec-butyl, and the term octyl includes n-octyl, 2-ethyl hexyl and neooctyl, among other isomers. Unless otherwise specified, any aryl group or arylalkyl group used herein includes all structural isomer (regioisomers, and linear or branched isomers), enantiomers, and diastereomers. For example, the term tolyl is meant to include any possible substituent position, that is, 2-methylphenyl, 3-methylphenyl, and/or 4-methylphenyl, and the term the term xylyl includes 2,3-dimethylphenyl, 2,4-dimethylphenyl, 2,5-dimethylphenyl, 2,6-dimethylphenyl, 3,4-dimethylphenyl, 3,5-dimethylphenyl, and 3,6-dimethylphenyl.

In an aspect, the alkyl, aryl, and alkyl aryl groups which may be employed as R, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ can be methyl, ethyl, n-propyl, iso-propyl, n-butyl, t-butyl, n-pentyl, neo-pentyl, phenyl, benzyl, tolyl, xylyl (dimethylphenyl), trimethylphenyl, phenylethyl, phenylpropyl, phenylbutyl, propyl-2-phenylethyl, and naphthyl. In an aspect, the alkyl groups which may be employed as R, $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be methyl, ethyl, n-propyl, iso-propyl, n-butyl, t-butyl, n-pentyl, and neo-pentyl; alternatively, methyl and ethyl; alternatively, methyl; or alternatively, ethyl. In an aspect, the aryl or aryl alkyl groups which may be employed as R, $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$ can be phenyl, benzyl, tolyl, xylyl (dimethylphenyl), trimethylphenyl, phenylethyl, phenylpropyl, phenylbutyl, and propyl-2-phenylethyl; alternatively, phenyl; alternatively, benzyl; alternatively, tolyl; or alternatively, xylyl.

Non-limiting examples of acyl groups that may be employed as R, $R^1$, $R^2$, $R^3$, and/or $R^4$ include a methanoyl group (—$C(O)CH_3$), an ethanoyl group (—$C(O)CH_2CH_3$), a n-propanoyl group (—$C(O)CH_2CH_2CH_3$), an iso-propanoyl group (—$C(O)CH(CH_3)_2$), a n-butanoyl group (—$C(O)CH_2CH_2CH_3$), a t-butanoyl group (—$C(O)C(CH_3)_3$), a n-pentanoyl group (—$C(O)CH_2CH_2CH_2CH_3$), a neo-pentanoyl group (—$C(O)CH_2C(CH_3)_3$), a benzoyl group (—$C(O)C_6H_5$), a toluoyl group (—$C(O)C_6H_4CH_3$), or a xyloyl group (—$C(O)C_6H_3(CH_3)_2$); alternatively, an ethanoyl group; alternatively, a propanoyl group; or alternatively, a benzoyl group. Non-limiting examples of hydrocarboxycarbonyl groups that may be employed as R, $R^1$, $R^2$, $R^3$, and/or $R^4$ include a methoxycarbonyl group (—$CO_2CH_3$), an ethoxycarbonyl group (—$CO_2CH_2CH_3$), a n-propoxycarbonyl group (—$CO_2CH_2CH_2CH_3$), an iso-propoxycarbonyl group (—$CO_2CH(CH_3)_2$), a n-butoxycarbonyl group (—$CO_2CH_2CH_2CH_2CH_3$), a t-butoxycarbonyl group (—$CO_2C(CH_3)_3$), a n-pentoxycarbonyl group (—$CO_2CH_2CH_2CH_2CH_2CH_3$), a neo-pentoxycarbonyl group (—$CO_2CH_2C(CH_3)_3$) group, a phenoxycarbonyl group (—$CO_2C_6H_5$), a benzoxycarbonyl group (—$CO_2CH_2C_6H_5$), a methylphenoxycarbonyl group (—$CO_2C_6H_4CH_3$), or a dimethylphenoxycarbonyl group (—$CO_2C_6H_3(CH_3)_2$); alternatively, a methoxycarbonyl group; alternatively, an ethoxycarbonyl group; or alternatively, a phenoxycarbonyl group. Non-limiting examples of N-hydrocarbylcarbamoyl groups that may be employed as R, $R^1$, $R^2$, $R^3$, and/or $R^4$ include a N-methylcarbamoyl group (—$C(O)NHCH_3$), a N-ethylcarbamoyl group (—$C(O)NHCH_2CH_3$), a N—N-propylcarbamoyl group (—$C(O)NHCH_2CH_2CH_3$), an N-iso-propylcarbamoyl group (—$C(O)NHCH(CH_3)_2$), a N-n-butylcarbamoyl group (—$C(O)NHCH_2CH_2CH_2CH_3$), a N-t-butylcarbamoyl group (—$C(O)NHC(CH_3)_3$), a N-n-pentylcarbamoyl group (—$C(O)NHCH_2CH_2CH_2CH_2CH_3$), a N-neo-pentylcarbamoyl group (—$C(O)NHCH_2C(CH_3)_3$), a N-phenylcarbamoyl group (—$C(O)NHC_6H_5$), a N-tolylcarbamoyl group (—$C(O)NHC_6H_4CH_3$), or a N-xylylcarbamoyl group (—$C(O)NHC_6H_3(CH_3)_2$); alternatively, a N-ethylcarbamoyl group; alternatively, a N-n-propylcarbamoyl group; or alternatively, a N-phenylcarbamoyl group. Non-limiting examples of N,N-dihydrocarbylcarbamoyl groups that may be employed as R, $R^1$, $R^2$, $R^3$, and/or $R^4$ include a N,N-dimethylcarbamoyl group (—$C(O)N(CH_3)_2$), a N,N-diethylcarbamoyl group (—$C(O)N(CH_2CH_3)_2$), a N,N-di-n-propylcarbamoyl group (—$C(O)N(CH_2CH_2CH_3)_2$), a N,N-di-iso-propylcarbamoyl group (—$C(O)N(CH(CH_3)_2)_2$), a N,N-di-n-butylcarbamoyl group (—$C(O)N(CH_2CH_2CH_2CH_3)_2$), a N,N-di-t-butylcarbamoyl group (—$C(O)N(C(CH_3)_3)_2$), a N,N-di-n-pentylcarbamoyl group (—$C(O)N(CH_2CH_2CH_2CH_2CH_3)_2$), a N,N-di-neo-pentylcarbamoyl group (—$C(O)N(CH_2C(CH_3)_3)_2$), a N,N-di-phenylcarbamoyl group (—$C(O)N(C_6H_5)_2$), a N,N-di-tolylcarbamoyl group (—$C(O)N(C_6H_4CH_3)_2$), or a N,N-di-xylylcarbamoyl group (—$C(O)N(C_6H_3(CH_3)_2)_2$); alternatively, a N,N-di-ethylcarbamoyl group; alternatively, a N,N-di-n-propylcarbamoyl group; or alternatively, a N,N-di-phenylcarbamoyl group.

Non-limiting examples of the organyl group having the structure —$(CH_2)_n$—Y, wherein Y is an halide, that may be employed as R, $R^1$, $R^2$, $R^3$, and/or $R^4$ include —$CH_2F$, —$CH_2Cl$, or —$CH_2Br$; alternatively, —$(CH_2)_2F$, —$(CH_2)_2Cl$, or —$(CH_2)_2Br$; alternatively, —$(CH_2)_2F$; or alternatively, —$(CH_2)_2Cl$. Non-limiting examples of the organyl group having the structure —$(CH_2)_n$—Y, wherein Y is $OR^9$, that may be employed as R, $R^1$, $R^2$, $R^3$, and/or $R^4$ include —$CH_2OCH_3$, —$CH_2OCH_2CH_3$, —CH$_2$OCH$_2$CH$_2$CH$_3$, —CH$_2$OCH(CH$_3$)$_2$, —CH$_2$OCH$_2$CH$_2$CH$_2$CH$_3$, —CH$_2$OC(CH$_3$)$_3$, —CH$_2$OCH$_2$CH$_2$CH$_2$CH$_2$CH$_3$, —CH$_2$OCH$_2$C(CH$_3$)$_3$, —CH$_2$OC$_6$H$_5$, —CH$_2$OC$_6$H$_4$CH$_3$, or —CH$_2$OC$_6$H$_3$(CH$_3$)$_2$; alternatively, —(CH$_2$)$_2$OCH$_3$, —(CH$_2$)$_2$OCH$_2$CH$_3$, —(CH$_2$)$_2$OCH$_2$CH$_2$CH$_3$, —(CH$_2$)$_2$OCH(CH$_3$)$_2$, —(CH$_2$)$_2$OCH$_2$CH$_2$CH$_2$CH$_3$, —(CH$_2$)$_2$OC(CH$_3$)$_3$, —(CH$_2$)$_2$OCH$_2$CH$_2$CH$_2$CH$_2$CH$_3$, —(CH$_2$)$_2$OCH$_2$C(CH$_3$)$_3$, —(CH$_2$)$_2$OC$_6$H$_5$, —(CH$_2$)$_2$OC$_6$H$_4$CH$_3$, or —(CH$_2$)$_2$OC$_6$H$_3$(CH$_3$)$_2$; alternatively, —CH$_2$OCH$_3$; alternatively, —CH$_2$OCH$_2$CH$_3$; alternatively, —CH$_2$OC$_6$H$_5$; alternatively, —(CH$_2$)$_2$OCH$_3$; alternatively, —(CH$_2$)$_2$OCH$_2$CH$_3$; or alternatively, —(CH$_2$)$_2$OC$_6$H$_5$. Non-limiting examples of the organyl group having the structure —(CH$_2$)$_n$—Y, wherein Y is SR$^{10}$, that may be employed as R, R$^1$, R$^2$, R$^3$, and/or R$^4$ include —CH$_2$SCH$_3$, —CH$_2$SCH$_2$CH$_3$, —CH$_2$SCH$_2$CH$_2$CH$_3$, —CH$_2$SCH(CH$_3$)$_2$, —CH$_2$SCH$_2$CH$_2$CH$_2$CH$_3$, —CH$_2$SC(CH$_3$)$_3$, —CH$_2$SCH$_2$CH$_2$CH$_2$CH$_2$CH$_3$, —CH$_2$SCH$_2$C(CH$_3$)$_3$, —CH$_2$SC$_6$H$_5$, —CH$_2$SC$_6$H$_4$CH$_3$, or —CH$_2$SC$_6$H$_3$(CH$_3$)$_2$; alternatively, —(CH$_2$)$_2$SCH$_3$, —(CH$_2$)$_2$SCH$_2$CH$_3$, —(CH$_2$)$_2$SCH$_2$CH$_2$CH$_3$, —(CH$_2$)$_2$SCH(CH$_3$)$_2$, —(CH$_2$)$_2$SCH$_2$CH$_2$CH$_2$CH$_3$, —(CH$_2$)$_2$SC(CH$_3$)$_3$, —(CH$_2$)$_2$SCH$_2$CH$_2$CH$_2$CH$_2$CH$_3$, —(CH$_2$)$_2$SCH$_2$C(CH$_3$)$_3$, —(CH$_2$)$_2$SC$_6$H$_5$, —(CH$_2$)$_2$SC$_6$H$_4$CH$_3$, or —(CH$_2$)$_2$SC$_6$H$_3$(CH$_3$)$_2$; alternatively, —CH$_2$SCH$_3$; alternatively, —CH$_2$SCH$_2$CH$_3$; alternatively, —CH$_2$SC$_6$H$_5$; alternatively, —(CH$_2$)$_2$SCH$_3$; alternatively, —(CH$_2$)$_2$SCH$_2$CH$_3$; or alternatively, —(CH$_2$)$_2$SC$_6$H$_5$. Non-limiting examples of the organyl group having the structure —(CH$_2$)$_n$—Y, wherein Y is NR$^{11}$R$^{12}$, that may be employed as R, R$^1$, R$^2$, R$^3$, and/or R$^4$ include —CH$_2$N(CH$_3$)$_2$, —CH$_2$N(CH$_2$CH$_3$)$_2$, —CH$_2$N(CH$_2$CH$_2$CH$_3$)$_2$, —CH$_2$N(CH(CH$_3$)$_2$)$_2$, —CH$_2$N(CH$_2$CH$_2$CH$_2$CH$_3$)$_2$, —CH$_2$N(C(CH$_3$)$_3$)$_2$, —CH$_2$N(CH$_2$CH$_2$CH$_2$CH$_2$CH$_3$)$_2$, —CH$_2$N(CH$_2$C(CH$_3$)$_3$)$_2$, —CH$_2$N(C$_6$H$_5$)$_2$, —CH$_2$N(C$_6$H$_4$CH$_3$)$_2$, or —CH$_2$N(C$_6$H$_3$(CH$_3$)$_2$)$_2$; alternatively, —(CH$_2$)$_2$N(CH$_3$)$_2$, —(CH$_2$)$_2$N(CH$_2$CH$_3$)$_2$, —(CH$_2$)$_2$N(CH$_2$CH$_2$CH$_3$)$_2$, —(CH$_2$)$_2$N(CH(CH$_3$)$_2$)$_2$, —(CH$_2$)$_2$N(CH$_2$CH$_2$CH$_2$CH$_3$)$_2$, —(CH$_2$)$_2$N(C(CH$_3$)$_3$)$_2$, —(CH$_2$)$_2$N(CH$_2$CH$_2$CH$_2$CH$_2$CH$_3$)$_2$, —(CH$_2$)$_2$N(CH$_2$C(CH$_3$)$_3$)$_2$, —(CH$_2$)$_2$N(C$_6$H$_5$)$_2$, —(CH$_2$)$_2$N(C$_6$H$_4$CH$_3$)$_2$, or —(CH$_2$)$_2$N(C$_6$H$_3$(CH$_3$)$_2$)$_2$; alternatively, —CH$_2$N(CH$_3$)$_2$; alternatively, —CH$_2$N(C$_6$H$_5$)$_2$; alternatively, —(CH$_2$)$_2$N(CH$_3$)$_2$; or alternatively, —(CH$_2$)$_2$N(C$_6$H$_5$)$_2$. Non-limiting examples of the organyl group having the structure —(CH$_2$)$_n$—Y, wherein Y is PR$^{11}$R$^{12}$, that may be employed as R, R$^1$, R$^2$, R$^3$, and/or R$^4$ include —CH$_2$P(CH$_3$)$_2$, —CH$_2$P(CH$_2$CH$_3$)$_2$, —CH$_2$P(CH$_2$CH$_2$CH$_3$)$_2$, —CH$_2$P(CH(CH$_3$)$_2$)$_2$, —CH$_2$P(CH$_2$CH$_2$CH$_2$CH$_3$)$_2$, —CH$_2$P(C(CH$_3$)$_3$)$_2$, —CH$_2$P(CH$_2$CH$_2$CH$_2$CH$_2$CH$_3$)$_2$, —CH$_2$P(CH$_2$C(CH$_3$)$_3$)$_2$, —CH$_2$P(C$_6$H$_5$)$_2$, —CH$_2$P(C$_6$H$_4$CH$_3$)$_2$, or —CH$_2$P(C$_6$H$_3$(CH$_3$)$_2$)$_2$; alternatively, —(CH$_2$)$_2$P(CH$_3$)$_2$, —(CH$_2$)$_2$P(CH$_2$CH$_3$)$_2$, —(CH$_2$)$_2$P(CH$_2$CH$_2$CH$_3$)$_2$, —(CH$_2$)$_2$P(CH(CH$_3$)$_2$)$_2$, —(CH$_2$)$_2$P(CH$_2$CH$_2$CH$_2$CH$_3$)$_2$, —(CH$_2$)$_2$P(C(CH$_3$)$_3$)$_2$, —(CH$_2$)$_2$P(CH$_2$CH$_2$CH$_2$CH$_2$CH$_3$)$_2$, —(CH$_2$)$_2$P(CH$_2$C(CH$_3$)$_3$)$_2$, —(CH$_2$)$_2$P(C$_6$H$_5$)$_2$, —(CH$_2$)$_2$P(C$_6$H$_4$CH$_3$)$_2$, or —(CH$_2$)$_2$P(C$_6$H$_3$(CH$_3$)$_2$)$_2$; alternatively, —CH$_2$P(CH$_3$)$_2$; alternatively, —CH$_2$P(C$_6$H$_5$)$_2$; alternatively, —(CH$_2$)$_2$P(CH$_3$)$_2$; or alternatively, —(CH$_2$)$_2$P(C$_6$H$_5$)$_2$.

In one aspect of the present invention, R and R$^1$ can independently be any C$_1$-C$_8$ hydrocarbyl group described herein and R$^2$, R$^3$, and R$^4$ are hydrogen. For example, R and R$^1$ can independently be any C$_1$-C$_8$ n-alkyl group described herein and R$^2$, R$^3$, and R$^4$ are hydrogen; alternatively, R can be any C$_1$-C$_8$ n-alkyl group described herein, R$^1$ can be any C$_1$-C$_8$ aryl or arylalkyl group described herein, and R$^2$, R$^3$, and R$^4$ are hydrogen; or alternatively, R can be any C$_1$-C$_8$ aryl or arylalkyl group described herein, R$^1$ can be any C$_1$-C$_8$ n-alkyl group described herein, and R$^2$, R$^3$, and R$^4$ are hydrogen. Examples include, but are not limited to, R and R$^1$ are methyl groups and R$^2$, R$^3$, and R$^4$ are hydrogen; alternatively, R and R$^1$ are ethyl groups and R$^2$, R$^3$, and R$^4$ are hydrogen; alternatively, R and R$^1$ are n-propyl groups and R$^2$, R$^3$, and R$^4$ are hydrogen; alternatively, R and R$^1$ are iso-propyl groups and R$^2$, R$^3$, and R$^4$ are hydrogen; alternatively, R and R$^1$ are phenyl groups and R$^2$, R$^3$, and R$^4$ are hydrogen; alternatively, R and R$^1$ are benzyl groups and R$^2$, R$^3$, and R$^4$ are hydrogen; alternatively, R is a methyl group, R$^1$ is an ethyl group, and R$^2$, R$^3$, and R$^4$ are hydrogen; alternatively, R is an ethyl group, R$^1$ is a methyl group, and R$^2$, R$^3$, and R$^4$ are hydrogen; alternatively, R is a methyl group, R$^1$ is a phenyl group, and R$^2$, R$^3$, and R$^4$ are hydrogen; alternatively, R is a phenyl group, R$^1$ is a methyl group, and R$^2$, R$^3$, and R$^4$ are hydrogen; alternatively, R is an ethyl group, R$^1$ is a phenyl group, and R$^2$, R$^3$, and R$^4$ are hydrogen; alternatively, R is a phenyl group, R$^1$ is an ethyl group, and R$^2$, R$^3$, and R$^4$ are hydrogen; alternatively, R is a methyl group, R$^1$ is a benzyl group, and R$^2$, R$^3$, and R$^4$ are hydrogen; alternatively, R is a benzyl group, R$^1$ is a methyl group, and R$^2$, R$^3$, and R$^4$ are hydrogen; alternatively, R is an ethyl group, R$^1$ is a benzyl group, and R$^2$, R$^3$, and R$^4$ are hydrogen; alternatively, R is a benzyl group, R$^1$ is an ethyl group, and R$^2$, R$^3$, and R$^4$ are hydrogen.

In another aspect of the present invention, R and R$^2$ can independently be any C$_1$-C$_8$ hydrocarbyl group described herein and R$^1$, R$^3$, and R$^4$ are hydrogen; or alternatively, R$^1$ and R$^3$ can independently be any C$_1$-C$_8$ hydrocarbyl group described herein and R, R$^2$, and R$^4$ are hydrogen. For example, R and R$^2$ can independently be a C$_1$-C$_8$ n-alkyl group described herein and R$^1$, R$^3$, and R$^4$ are hydrogen; alternatively, R$^1$ and R$^3$ can independently be any C$_1$-C$_8$ n-alkyl group described herein and R, R$^2$, and R$^4$ are hydrogen; alternatively, R can be any C$_1$-C$_8$ n-alkyl group described herein, R$^2$ can be any C$_1$-C$_8$ aryl or arylalkyl group described herein, and R$^1$, R$^3$, and R$^4$ are hydrogen; alternatively, R$^1$ can be any C$_1$-C$_8$ n-alkyl group described herein, R$^3$ can be any C$_1$-C$_8$ aryl or arylalkyl group described herein, and R, R$^2$, and R$^4$ are hydrogen; alternatively, R and R$^2$ can be any C$_1$-C$_8$ aryl or arylalkyl group described herein and R$^1$, R$^3$, and R$^4$ are hydrogen; or alternatively, R$^1$ and R$^3$ can be any C$_1$-C$_8$ aryl or arylalkyl group described herein and R, R$^2$, and R$^4$ are hydrogen. Examples include, but are not limited to, R and R$^2$ are methyl groups and R$^1$, R$^3$, and R$^4$ are hydrogen; alternatively, R$^1$ and R$^3$ are methyl groups and R, R$^3$, and R$^4$ are hydrogen; alternatively, R and R$^2$ are ethyl groups and R$^1$, R$^3$, and R$^4$ are hydrogen; alternatively, R$^1$ and R$^3$ are ethyl groups and R, R$^3$, and R$^4$ are hydrogen; alternatively, R is a methyl group, R$^2$ is an ethyl group, and R$^1$, R$^3$, and R$^4$ are hydrogen; alternatively, R$^1$ is an ethyl group, R$^3$ is a methyl group, and R, R$^3$, and R$^4$ are hydrogen; alternatively, R is an ethyl group, R$^2$ is a methyl group, and R$^1$, R$^3$, and R$^4$ are hydrogen; or alternatively, R$^1$ is a methyl group, R$^3$ is an ethyl group, and R, R$^3$, and R$^4$ are hydrogen.

In yet another aspect, R, R$^1$, and R$^3$ can independently be any C$_1$-C$_8$ hydrocarbyl group described herein and R$^2$ and R$^4$ are hydrogen; alternatively, R, R$^1$, and R$^2$ can independently be any C$_1$-C$_8$ hydrocarbyl group described herein and R$^3$ and R$^4$ are hydrogen. For example, R, R$^1$, and R$^3$ can independently be any C$_1$-C$_8$ n-alkyl group described herein and R$^2$ and R$^4$ are hydrogen; alternatively, R, R$^1$, and R$^2$ can independently be any C$_1$-C$_8$ n-alkyl group described herein and R$^3$ and R$^4$ are hydrogen. Examples include, but are not limited to, R, R$^1$, and R$^3$ are methyl groups and R$^3$ and R$^4$ are hydrogen; alternatively, R, R$^1$, and R$^2$ are methyl groups and R$^3$ and $R^4$ are hydrogen; alternatively, R, $R^1$, and $R^3$ are ethyl groups and $R^3$ and $R^4$ are hydrogen; alternatively, R, $R^1$, and $R^2$ are ethyl groups and $R^3$ and $R^4$ are hydrogen; alternatively, R and $R^1$ are ethyl groups, $R^2$ is a methyl group, and $R^3$ and $R^4$ are hydrogen; or alternatively, R and $R^1$ are methyl groups, $R^2$ is an ethyl group, and $R^3$ and $R^4$ are hydrogen.

In still another aspect, R, $R^1$, $R^2$ and $R^3$ can independently be any $C_1$-$C_8$ hydrocarbyl group described herein and $R^4$ is hydrogen. For example, R, $R^1$, $R^2$ and $R^3$ can independently be any $C_1$-$C_8$ n-alkyl group described herein and $R^4$ is hydrogen; alternatively, R, $R^1$, $R^2$ and $R^3$ can independently be any $C_1$-$C_8$ aryl or arylalkyl group described herein and $R^4$ is hydrogen; alternatively, R and $R^1$ can independently be any n-alkyl group described herein, $R^2$ and $R^3$ can independently be any $C_1$-$C_8$ aryl or arylalkyl group described herein, and $R^4$ is hydrogen; or alternatively, R and $R^1$ can independently be any $C_1$-$C_8$ aryl or arylalkyl group described herein, $R^2$ and $R^3$ can independently be any $C_1$-$C_8$ n-alkyl group described herein, and $R^4$ is hydrogen. Examples include, but are not limited to, R, $R^1$, $R^2$ and $R^3$ are methyl groups and $R^4$ is hydrogen; alternatively, R, $R^1$, $R^2$ and $R^3$ are ethyl groups and $R^4$ is hydrogen; R and $R^1$ are ethyl groups, $R^2$ and $R^3$ are methyl groups, and $R^4$ is hydrogen; alternatively, R and $R^1$ are methyl groups, $R^2$ and $R^3$ are ethyl groups, and $R^4$ is hydrogen; or alternatively, R and $R^1$ are benzyl groups, $R^2$ and $R^3$ are methyl groups, and $R^4$ is hydrogen.

In a further aspect, R can be any $C_1$-$C_{18}$ organyl group or $C_1$-$C_8$ organyl group described herein and $R^1$, $R^2$, $R^3$, and $R^4$ are hydrogen; alternatively, $R^1$ can be any $C_1$-$C_{18}$ organyl group or $C_1$-$C_8$ organyl group described herein and R, $R^2$, $R^3$, and $R^4$ are hydrogen; alternatively, R can be any $C_1$-$C_8$ hydrocarbyl group described herein, $R^1$ can be any $C_1$-$C_{18}$ organyl group or $C_1$-$C_8$ organyl group described herein, and $R^2$, $R^3$, and $R^4$ are hydrogen; or alternatively, R can independently be any $C_1$-$C_{18}$ organyl group or $C_1$-$C_8$ organyl group described herein, $R^1$ can be any $C_1$-$C_8$ hydrocarbyl group described herein, and $R^2$, $R^3$, and $R^4$ are hydrogen. For example, R can be any acyl group, hydrocarboxycarbonyl group, carbamoyl group, N-hydrocarbylcarbamoyl group, N,N-dihydrocarbylcarbamoyl group, or organyl group having the structure —$(CH_2)_n$—Y described herein, and $R^1$, $R^2$, $R^3$, and $R^4$ are hydrogen; alternatively, $R^1$ can be any acyl group, hydrocarboxycarbonyl group, carbamoyl group, N-hydrocarbylcarbamoyl group, N,N-dihydrocarbylcarbamoyl group, or organyl group having the structure —$(CH_2)_n$—Y described herein, and R, $R^2$, $R^3$, and $R^4$ are hydrogen; alternatively, R can be any $C_1$-$C_8$ n-alkyl group described herein, $R^1$ can be any acyl group, hydrocarboxycarbonyl group, carbamoyl group, N-hydrocarbylcarbamoyl group, N,N-dihydrocarbylcarbamoyl group, or organyl group having the structure —$(CH_2)_n$—Y described herein, and $R^2$, $R^3$, and $R^4$ are hydrogen; or alternatively, R can be any acyl group, hydrocarboxycarbonyl group, carbamoyl group, N-hydrocarbylcarbamoyl group, N,N-dihydrocarbylcarbamoyl group, or organyl group having the structure —$(CH_2)_n$—Y described herein, $R^1$ can be any $C_1$-$C_8$ n-alkyl group described herein, and $R^2$, $R^3$, and $R^4$ are hydrogen; alternatively, R can be any $C_1$-$C_8$ aryl or arylalkyl group described herein, $R^1$ can be any acyl group, hydrocarboxycarbonyl group, carbamoyl group, N-hydrocarbylcarbamoyl group, N,N-dihydrocarbylcarbamoyl group, or organyl group having the structure —$(CH_2)_n$—Y described herein, $R^1$ can be any $C_1$-$C_8$ aryl or arylalkyl group described herein, and $R^2$, $R^3$, and $R^4$ are hydrogen.

In yet a further aspect, R and $R^1$ can independently be any $C_1$-$C_{18}$ organyl group or $C_1$-$C_8$ organyl group having the structure —$(CH_2)_n$—Y described herein and $R^2$, $R^3$, and $R^4$ are hydrogen. For example, R and $R^1$ can independently be any organyl group having the structure —$(CH_2)_n$—Y, wherein Y is an halide and n is any positive integer described herein, and $R^2$, $R^3$, and $R^4$ are hydrogen; alternatively, R and $R^1$ can independently be any organyl group having the structure —$(CH_2)_n$—$OR^9$, wherein $R^9$ can be any hydrocarbyl group described herein and n is any positive integer described herein, and $R^2$, $R^3$, and $R^4$ are hydrogen; alternatively, R and $R^1$ can independently be any organyl group having the structure —$(CH_2)_n$—$SR^{10}$, wherein $R^{10}$ can be any hydrocarbyl group described herein and n is any positive integer described herein, and $R^2$, $R^3$, and $R^4$ are hydrogen; alternatively, R and $R^1$ can independently be any organyl group having the structure —$(CH_2)_n$—$NR^{11}R^{12}$, wherein $R^{11}$ and $R^{12}$ can be any hydrocarbyl group described herein and n is any positive integer described herein, and $R^2$, $R^3$, and $R^4$ are hydrogen; or alternatively, R and $R^1$ can independently be any organyl group having the structure —$(CH_2)_n$—$PR^{13}R^{14}$, wherein $R^{13}$ and $R^{14}$ can be any hydrocarbyl group described herein and n is any positive integer described herein, and $R^2$, $R^3$, and $R^4$ are hydrogen. Examples include, but are not limited to, R and $R^1$ are —$CH_2F$, —$CH_2Cl$, or —$CH_2Br$ and $R^2$, $R^3$, and $R^4$ are hydrogen; alternatively, R and $R^1$ are —$(CH_2)_2F$, —$(CH_2)_2Cl$, or —$(CH_2)_2Br$ and $R^2$, $R^3$, and $R^4$ are hydrogen; alternatively, R and $R^1$ are —$(CH_2)_2Cl$ and $R^2$, $R^3$, and $R^4$ are hydrogen; or alternatively, R and $R^1$ are —$(CH_2)_2F$ and $R^2$, $R^3$, and $R^4$ are hydrogen. Other examples include, but are not limited to, R and $R^1$ are —$CH_2OCH_3$ or —$CH_2OCH_2CH_3$ and $R^2$, $R^3$, and $R^4$ are hydrogen; alternatively, R and $R^1$ are —$(CH_2)_2OCH_3$ or —$(CH_2)_2OCH_2CH_3$ and $R^2$, $R^3$, and $R^4$ are hydrogen; alternatively R and $R^1$ are —$CH_2OCH_3$ and $R^2$, $R^3$, and $R^4$ are hydrogen; alternatively, R and $R^1$ are —$CH_2OCH_2CH_3$ and $R^2$, $R^3$, and $R^4$ are hydrogen; alternatively, R and $R^1$ are —$(CH_2)_2OCH_3$ and $R^2$, $R^3$, and $R^4$ are hydrogen; alternatively, R and $R^1$ are —$(CH_2)_2OCH_2CH_3$ and $R^2$, $R^3$, and $R^4$ are hydrogen; alternatively, R and $R^1$ are —$CH_2OC_6H_5$ and $R^2$, $R^3$, and $R^4$ are hydrogen; or alternatively, R and $R^1$ are —$(CH_2)_2OC_6H_5$ and $R^2$, $R^3$, and $R^4$ are hydrogen. Additional examples include, but are not limited to, R and $R^1$ are —$CH_2SCH_3$ or —$CH_2SCH_2CH_3$ and $R^2$, $R^3$, and $R^4$ are hydrogen; alternatively, R and $R^1$ are —$(CH_2)_2SCH_3$ or —$(CH_2)_2SCH_2CH_3$ and $R^2$, $R^3$, and $R^4$ are hydrogen; alternatively R and $R^1$ are —$CH_2SCH_3$ and $R^2$, $R^3$, and $R^4$ are hydrogen; alternatively, R and $R^1$ are —$CH_2SCH_2CH_3$ and $R^2$, $R^3$, and $R^4$ are hydrogen; alternatively, R and $R^1$ are —$(CH_2)_2SCH_3$ and $R^2$, $R^3$, and $R^4$ are hydrogen; alternatively, R and $R^1$ are —$(CH_2)_2SCH_2CH_3$ and $R^2$, $R^3$, and $R^4$ are hydrogen; alternatively, R and $R^1$ are —$CH_2SC_6H_5$ and $R^2$, $R^3$, and $R^4$ are hydrogen; or alternatively, R and $R^1$ are —$(CH_2)_2SC_6H_5$ and $R^2$, $R^3$, and $R^4$ are hydrogen. Further examples include, but are not limited to, R and $R^1$ are —$CH_2N(CH_3)_2$ or —$CH_2N(CH_2CH_3)_2$, and $R^2$, $R^3$, and $R^4$ are hydrogen; alternatively, R and $R^1$ are —$(CH_2)_2N(CH_3)_2$ or —$(CH_2)_2N(CH_2CH_3)_2$ and $R^2$, $R^3$, and $R^4$ are hydrogen; alternatively R and $R^1$ are —$CH_2N(CH_3)_2$ and $R^2$, $R^3$, and $R^4$ are hydrogen; alternatively, R and $R^1$ are —$CH_2N(CH_2CH_3)_2$ and $R^2$, $R^3$, and $R^4$ are hydrogen; alternatively, R and $R^1$ are —$(CH_2)_2N(CH_3)_2$ and $R^2$, $R^3$, and $R^4$ are hydrogen; alternatively, R and $R^1$ are —$(CH_2)_2N(CH_2CH_3)_2$ and $R^2$, $R^3$, and $R^4$ are hydrogen; alternatively, R and $R^1$ are —$CH_2N(C_6H_5)_2$ and $R^2$, $R^3$, and $R^4$ are hydrogen; or alternatively, R and $R^1$ are —$(CH_2)_2N(C_6H_5)_2$ and $R^2$, $R^3$, and $R^4$ are hydrogen. Also, further examples can include, but are not limited to, R and $R^1$ are —$CH_2P(CH_3)_2$ or —$CH_2P(CH_2CH_3)_2$, and $R^2$, $R^3$, and $R^4$ are hydrogen; alternatively, R and $R^1$ are —$(CH_2)_2P(CH_3)_2$ or —$(CH_2)_2P(CH_2CH_3)_2$ and $R^2$, $R^3$, and $R^4$ are hydrogen; alternatively R and $R^1$ are —$CH_2P(CH_3)_2$ and $R^2$, $R^3$, and $R^4$ are hydrogen; alternatively, R and $R^1$ are —$CH_2P(CH_2CH_3)_2$ and $R^2$, $R^3$, and $R^4$ are hydrogen; alternatively, R and $R^1$ are —$(CH_2)_2P(CH_3)_2$ and $R^2$, $R^3$, and $R^4$ are hydrogen; alternatively, R and $R^1$ are —$(CH_2)_2P(CH_2CH_3)_2$ and $R^2$, $R^3$, and $R^4$ are hydrogen; alternatively, R and $R^1$ are —$CH_2P(C_6H_5)_2$ and $R^2$, $R^3$, and $R^4$ are hydrogen; or alternatively, R and $R^1$ are —$(CH_2)_2P(C_6H_5)_2$ and $R^2$, $R^3$, and $R^4$ are hydrogen.

In the process for producing a γ-nitrocarbonyl compound, a primary or secondary nitro compound, an α,β-unsaturated carbonyl compound, a base, and water are contacted. Typically, the molar ratio of the total moles of the primary or secondary nitro compound to the total moles of the α,β-unsaturated carbonyl compound is greater than about 1:1, such as, for example, greater than about 1.025:1, greater than about 1.05:1, or greater than about 1.075:1. This molar ratio can be within a range from about 1.025:1 to about 1.5:1, from about 1.05:1 to about 1.2:1, or from about 1.075:1 to about 1.15:1, in some aspects of this invention.

In the initial reaction mixture containing a primary or secondary nitro compound, an α,β-unsaturated carbonyl compound, a base, and water, the initial concentration of the base can fall within a range from about 2 to about 8 equivalents per liter. For example, the initial concentration of the base can be about 2.3, about 2.6, or about 2.9 equivalents per liter. In an aspect, the initial concentration of the base can range from about 2.3 to about 6, from about 2.6 to 5, or from about 2.9 to about 4 equivalents per liter. The initial effective concentration of the primary or secondary nitro compound in the initial reaction mixture often is greater than about 1 molar. In some aspects of this invention, the initial effective concentration of the primary or secondary nitro compound is greater than about 1.15 molar, greater than about 1.3 molar, or greater than about 1.45 molar. In another aspect, the initial effective concentration of the primary or secondary nitro compound ranges from about 1.15 molar to about 4 molar, from about 1.3 molar to 3 molar, or from about 1.45 molar to 2.5 molar.

According to one aspect of the present invention, a γ-nitrocarbonyl compound is produced by first forming a mixture of a base, a primary or secondary nitro compound, and water. Then, this mixture is contacted with an α,β-unsaturated carbonyl compound to produce the γ-nitrocarbonyl compound in a yield of at least about 75 mole %. In such an aspect, the process for producing a γ-nitrocarbonyl compound can comprise (or alternatively, consistent essentially of, or consist of) the following steps:

a) forming a mixture comprising (or alternatively, consisting essentially of, or consisting of) a base, a primary or secondary nitro compound, and water;

b) contacting a α,β-unsaturated carbonyl compound with the mixture; and c) forming the γ-nitrocarbonyl compound in a yield of at least about 75 mole %.

In this aspect, the same initial concentration of the base and the initial effective concentration of the primary or secondary nitro compound as discussed herein would apply, except that the concentrations would be based on the mixture of the base, the primary or secondary nitro compound, and water, excluding any contribution due to the α,β-unsaturated carbonyl compound. Also, in this aspect, the reaction times and temperatures disclosed above are directed to the step in the process where the mixture of the base, the primary or secondary nitro compound, and water is contacted with the α,β-unsaturated carbonyl compound to form the γ-nitrocarbonyl compound. For instance, the mixture of the base, the primary or secondary nitro compound, and water can be formed at a different temperature than the reaction with the α,β-unsaturated carbonyl compound is conducted. This mixture also can be stored for a period of time prior to contacting and reacting it with the α,β-unsaturated carbonyl compound, but the storage time of the mixture is not included in the contemplated reaction time. Once the mixture of the base, the primary or secondary nitro compound, and water is contacted with the α,β-unsaturated carbonyl compound, the reaction to produce the γ-nitrocarbonyl compound should be conducted, generally, in a time period ranging from about 1 minute to about 2 hours, ranging from about 1 minute to about 90 minutes, ranging from about 5 minutes to about 75 minutes, ranging from about 5 minutes to about 60 minutes, ranging from about 5 minutes to about 45 minutes, or ranging from about 5 minutes to about 30 minutes.

Synthesizing γ-Dicarbonyl Compounds from γ-Nitrocarbonyl Compounds

Processes for producing γ-dicarbonyl compounds are provided in the present invention. One such process can comprise (or alternatively, consistent essentially of, or consist of) the following steps:

a) contacting a γ-nitrocarbonyl compound, a peroxide compound, a base, and water, wherein a molar ratio of the peroxide compound to the γ-nitrocarbonyl compound is in a range from about 1:1 to about 15:1; and b) forming the γ-dicarbonyl compound.

Generally, to be able to form the γ-dicarbonyl compound, the γ-nitrocarbonyl compound utilized must have a hydrogen atom on the carbon atom bearing the nitro group.

As with the process for synthesizing a γ-nitrocarbonyl compound provided above, the process for synthesizing a γ-dicarbonyl compound can be conducted under an inert atmosphere (e.g., a nitrogen or argon atmosphere, among other possibilities), although this is not a requirement. Moreover, this process can be conducted at a variety of reaction temperatures, typically ranging from about 20° C. to about 100° C. In some aspects of this invention, the process is conducted at a temperature in a range from about 40° C. to about 100° C., or from about 50° C. to about 90° C.

The appropriate reaction time for the synthesis of a γ-dicarbonyl compound can depend greatly upon the reaction temperature and reagent concentrations that are selected. Often, the process to produce a γ-dicarbonyl compound is conducted in a time period ranging from about 5 minutes to about 10 hours, or ranging from about 5 minutes to about 8 hours. For instance, reaction times to produce the γ-dicarbonyl compound ranging from about 10 minutes to about 6 hours, ranging from about 10 minutes to about 4 hours, ranging from about 15 minutes to about 3 hours, or ranging from about 15 minutes to about 2 hours, can be employed.

The process for synthesizing a γ-dicarbonyl compound can produce the γ-dicarbonyl compound in a yield of at least about 70 mole %. More often, the yield of the γ-dicarbonyl compound is at least about 75 mole %. In another aspect, the yield of the γ-dicarbonyl compound is at least about 80 mole %, or alternatively, at least about 85 mole %. In yet another aspect, the yield of the γ-dicarbonyl compound is at least about 90 mole %. These yields are based on the moles of the limiting reactant, for instance, the moles of the γ-nitrocarbonyl compound.

In step a) of the process, a γ-nitrocarbonyl compound, a peroxide compound, a base, and water are contacted. The base employed in this process can be the same as that employed in the synthesis of the γ-nitrocarbonyl compound, discussed above. Hence, the base can be an alkali metal carbonate or an alkaline earth metal carbonate, suitable examples of which include, but are not limited to, lithium carbonate, sodium carbonate, potassium carbonate, magnesium carbonate, calcium carbonate, and the like, or combinations thereof. The base used in the synthesis of the γ-dicarbonyl compound can be an alkali metal carbonate and, in one aspect of this invention, the base is potassium carbonate.

A peroxide compound is employed in the process to produce the γ-dicarbonyl compound. The peroxide compound may be hydrogen peroxide, an organic peroxide, an alkali metal peroxide, or an alkaline metal peroxide. Non-limiting examples of organic peroxides include $C_2$ to $C_{30}$ peracids, alkylhydroperoxides, dialkylperoxides, peresters, peracetals, perketals, or combinations thereof. Non-limiting examples of suitable alkali peroxide compounds include sodium peroxide and potassium peroxide. Non-limiting examples of alkaline peroxides include calcium peroxide and magnesium peroxide, or combinations of more than one of these compounds. In one aspect of the present invention, the peroxide compound is hydrogen peroxide. Generally, the hydrogen peroxide is utilized in the form of an aqueous solution. Aqueous hydrogen peroxide solutions which may be utilized in the process for producing a γ-dicarbonyl compound include, but are not limited to, 20 to 50 weight percent solutions of hydrogen peroxide. Depending upon the desired initial hydrogen peroxide concentration, the desired initial effective γ-nitrocarbonyl compound concentration, or desired effective hydrogen peroxide to γ-nitrocarbonyl compound ratio, the final concentration of the hydrogen peroxide may be different than the concentration of the hydrogen peroxide solution utilized to form the reaction mixture.

In some aspects of this invention, the γ-nitrocarbonyl compound has the following formula:

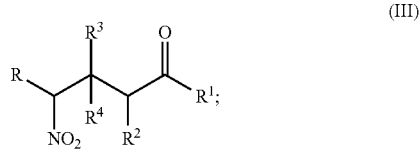

(III)

and the γ-dicarbonyl compound has the formula:

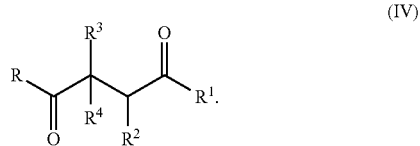

(IV)

Formulas (III), and (IV) are not designed to show stereochemistry or isomeric positioning of the different moieties (e.g., these formulas are not intended to show cis or trans isomers), although such compounds are contemplated and encompassed by these formulas. R, $R^1$, $R^2$, $R^3$, and $R^4$ have been described herein and can be utilized to describe aspects of the method for synthesizing a γ-dicarbonyl compound having formula (IV) from the γ-nitrocarbonyl compound having formula (III).

In the process for producing a γ-dicarbonyl compound, a γ-nitrocarbonyl compound, a peroxide compound, a base, and water are contacted. Generally, the molar ratio of the total moles of the peroxide compound to the total moles of the γ-nitrocarbonyl compound is less than about 15:1. The molar ratio can be in a range of, for example, from about 0.8:1 to about 12:1, from about 1:1 to about 10:1, from about 1:1 to about 8:1, or from about 1:1 to about 6:1. Molar ratios of the moles of peroxide compound to the moles of γ-nitrocarbonyl compound in a range from about 1:1 to about 5:1, or from about 1:1 to about 3:1, also are encompassed by this invention.

The initial effective concentration of the γ-nitrocarbonyl compound in the initial reaction mixture—that is, containing the γ-nitrocarbonyl compound, the peroxide compound, the base, and water—often is greater than about 0.25 molar. In one aspect, the initial effective concentration of the γ-nitrocarbonyl compound is greater than about 0.5 molar, greater than about 0.7 molar, or greater than about 0.9 molar. In another aspect, the initial effective concentration of the γ-nitrocarbonyl compound is in a range from about 0.25 to about 3 molar, for example, from about 0.5 to about 2.5 molar. Yet, in another aspect, the initial effective concentration of the γ-nitrocarbonyl compound is in range from about 0.7 to about 2 molar, or from about 0.9 to about 1.5 molar. In this context, the initial effective concentration refers to the total concentration of the γ-nitrocarbonyl compound and the anion of the γ-nitrocarbonyl compound (which is produced via the reaction of the γ-nitrocarbonyl compound with the base).

According to one aspect of this invention, the contacting of the γ-nitrocarbonyl compound, the peroxide compound, the base, and water results in an exotherm. Often, the γ-nitrocarbonyl compound, the peroxide compound, the base, and water are contacted at a temperature in a range from about 20° C. to about 30° C., or at about 25° C. (i.e., room temperature). If the temperature of the reaction system is not controlled, the reaction exotherm will increase the temperature of the reaction mixture. It is contemplated that the reaction exotherm can result in a temperature that is within a range from about 40° C. to about 100° C., or from about 50° C. to about 90° C.

According to another aspect of the present invention, a γ-nitrocarbonyl compound, a peroxide compound, a base, and water are contacted at a total molar ratio of the peroxide compound to the γ-nitrocarbonyl compound of from about 1:1 to about 15:1, a γ-dicarbonyl compound is formed, and the resultant γ-dicarbonyl compound is subsequently isolated from the aqueous reaction mixture. One method for isolating the γ-dicarbonyl compound includes an extraction of the γ-dicarbonyl compound from the aqueous reaction mixture with an organic solvent. Illustrative solvent types can include, for example, aromatic hydrocarbons, aliphatic hydrocarbons, organic ethers, organic carbonates, organic esters, organic ketones, organic aldehydes, halogenated aliphatic hydrocarbons, aromatic hydrocarbons, halogenated aromatic hydrocarbons, and combinations thereof. Aliphatic hydrocarbons which may be useful as a solvent include $C_4$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and combinations thereof. Non-limiting examples of suitable cyclic aliphatic solvents include cyclohexane, methyl cyclohexane, and combinations thereof. Aromatic hydrocarbons which may be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. Organic ethers, organic carbonates, organic esters, organic ketones, or organic aldehydes which may be useful as a solvent include $C_2$ to $C_{20}$ organic ethers, organic carbonates, organic esters, organic ketones, or organic aldehydes; alternatively, $C_2$ to $C_{10}$ organic ethers, organic carbonates, organic esters, organic ketones, or organic aldehydes; or alternatively, $C_2$ to $C_5$ organic ethers, organic carbonates, organic esters, organic ketones, or organic aldehydes. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. Non-limiting examples of suitable organic carbonates which may be utilized as a solvent include ethylene carbonate, propylene carbonate, diethyl carbonate, diethyl carbonate, and combinations thereof. Non-limiting examples of suitable esters which may be utilized as a solvent include ethyl acetate, propyl acetate, butyl acetate, isobutyl isobutyrate, and combinations thereof. Non-limiting examples of suitable ketones which may be utilized as a solvent include acetone, ethyl methyl ketone, and combinations thereof. Halogenated aliphatic hydrocarbons which may be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. Non-limiting examples of such halogenated aliphatic hydrocarbons which may be utilized as a solvent include carbon tetrachloride, chloroform, methylene chloride, dichloroethane, trichloroethane, and combinations thereof. Halogenated aromatic hydrocarbons which may be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof. In particular, the halogenated organic solvent used to extract the γ-dicarbonyl compound from the aqueous reaction mixture can be dichloromethane.

In yet another aspect of the present invention, a γ-dicarbonyl compound is produced by first forming a mixture of a base, a γ-nitrocarbonyl compound, and water. Then, this mixture is contacted with a peroxide compound, at a molar ratio of the peroxide compound to the γ-nitrocarbonyl ranging from about 1:1 to about 15:1. This process results in the formation of the desired γ-dicarbonyl compound. In such an aspect, the process for producing a γ-dicarbonyl compound can comprise (or alternatively, consistent essentially of, or consist of) the following steps:

a) forming a mixture comprising (or alternatively, consisting essentially of, or consist of) a base, a γ-nitrocarbonyl compound, and water;

b) contacting a peroxide compound with the mixture; and c) forming the γ-dicarbonyl compound.

In this aspect, the same initial effective concentration of the γ-nitrocarbonyl as discussed herein would apply, except that the concentration would be based on the mixture of the base, the γ-nitrocarbonyl compound, and water, excluding any contribution due to the peroxide compound. Also, in this aspect, the reaction times and temperatures disclosed above are directed to the step in the process where the mixture of the base, the γ-nitrocarbonyl compound, and water is contacted with the peroxide compound to form the γ-dicarbonyl compound. For example, the mixture of the base, the γ-nitrocarbonyl, and water can be formed at a different temperature than the reaction with the peroxide compound is conducted. This mixture also can be stored for a period of time prior to contacting and reacting it with the peroxide compound, but the storage time of the mixture is not included in the contemplated reaction time. Once the mixture of the base, the γ-nitrocarbonyl compound, and water is contacted with the peroxide compound, this reaction to produce the γ-dicarbonyl compound should be conducted, generally, in a time period ranging from about 5 minutes to about 10 hours, ranging from about 5 minutes to about 8 hours, ranging from about 10 minutes to about 6 hours, ranging from about 10 minutes to about 4 hours, ranging from about 15 minutes to about 3 hours, or ranging from about 15 minutes to about 2 hours.

Synthesizing γ-Dicarbonyl Compounds from α,β-Unsaturated Carbonyl Compounds

Another process for producing a γ-dicarbonyl compound is provided in the present invention and, in this process, the starting materials are an α,β-unsaturated carbonyl compound and a primary nitro compound. This process comprises (or alternatively, consists essentially of, or consists of) the following steps:

a) contacting a primary nitro compound, an α,β-unsaturated carbonyl compound, a base, and water to produce a γ-nitrocarbonyl compound; and b) contacting a peroxide compound with the γ-nitrocarbonyl compound at a molar ratio of the peroxide compound to the γ-nitrocarbonyl compound in a range from about 1:1 to about 15:1 to produce the γ-dicarbonyl compound.

It is contemplated that both step a) and step b) can be conducted in a single reactor. That is, this process can be a one-pot synthesis of a γ-dicarbonyl compound from an α,β-unsaturated carbonyl compound, wherein the peroxide compound is added at an appropriate time and the γ-nitrocarbonyl compound is not isolated. However, in another embodiment, the process for producing the γ-dicarbonyl compound from an α,β-unsaturated carbonyl compound may include isolation, and in other embodiments purification, of the γ-nitrocarbonyl compound.

As with the processes for synthesizing a γ-nitrocarbonyl compound and a γ-dicarbonyl provided above, this process for synthesizing a γ-dicarbonyl compound can be conducted under an inert atmosphere (e.g., a nitrogen or argon atmosphere, among other possibilities), although this is not a requirement. Additionally, this process for producing a γ-dicarbonyl compound from an α,β-unsaturated carbonyl compound can employ the same temperatures that were discussed above for the respective steps of synthesizing a γ-nitrocarbonyl compound and synthesizing a γ-dicarbonyl compound from a γ-nitrocarbonyl compound.

The reaction time for this process for producing a γ-dicarbonyl compound (for example, in a one-pot synthesis) can vary significantly depending upon the reaction temperatures and reagent concentrations that are selected. Generally, the process—inclusive of both step a) and step b)—is conducted in a time period ranging from about 5 minutes to about 10 hours. Reaction times to produce the γ-dicarbonyl compound ranging from about 5 minutes to about 8 hours, from about 10 minutes to about 6 hours, or from about 15 minutes to about 4 hours, can be employed. In this and other aspects of the invention, the reaction time for the process to produce the γ-dicarbonyl compound can be within a range from about 20 minutes to about 3 hours such as, for example, conducting the synthesis of the γ-dicarbonyl compound from the α,β-unsaturated carbonyl compound in a time period ranging from about 20 minutes to about 2 hours.

As discussed above, step a) of this process can be implemented by first forming a mixture of a base, a primary nitro compound, and water. Then, this mixture can be contacted with an α,β-unsaturated carbonyl compound to produce the γ-nitrocarbonyl compound. If the γ-nitrocarbonyl compound is produced in this manner, then the reaction time disclosed herein does not include the time period for the formation of the mixture of the base, the primary nitro compound, and water, prior to the contacting of this mixture with the α,β-unsaturated carbonyl compound.

Step a) of the synthesis produces a γ-nitrocarbonyl compound in a yield of at least about 75 mole %. Often, the yield of the γ-nitrocarbonyl compound is at least about 80 mole %, at least about 85 mole %, or at least about 90 mole %. The overall yield of a γ-dicarbonyl compound in this process can be at least about 70 mole %. It is also contemplated that the yield of the γ-dicarbonyl compound in this process can be at least about 75 mole %, at least about 80 mole %, or at least about 85 mole %. The yield of the γ-dicarbonyl compound is at least about 90 mole % in one aspect of this invention. These yields are based on the moles of the limiting reactant, which often times is the α,β-unsaturated carbonyl compound.

In accordance with some aspects of the present invention, the primary nitro compound can be a nitroalkane having the formula:

(I)

the α,β-unsaturated carbonyl compound can have the formula:

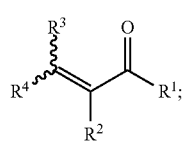
(II)

and the γ-dicarbonyl compound can have the formula:

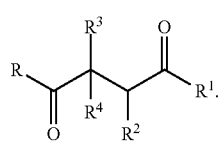
(IV)

Formulas (I), (II), and (IV) are not designed to show stereochemistry or isomeric positioning of the different moieties (e.g., these formulas are not intended to show cis or trans isomers), although such compounds are contemplated and encompassed by these formulas. R, $R^1$, $R^2$, $R^3$, and $R^4$ have been described herein and can be utilized to describe aspects of the method for synthesizing a γ-dicarbonyl compound having formula (IV) from the nitroalkane having formula (I) and the α,β-unsaturated carbonyl compound having formula (II).

In this process for producing a γ-dicarbonyl compound from an α,β-unsaturated carbonyl compound (for example, in a one-pot synthesis), the same initial effective concentration of the primary nitro compound, molar ratio of the primary nitro compound to the α,β-unsaturated carbonyl compound, and molar ratio of the peroxide compound to the γ-nitrocarbonyl compound can be employed as discussed herein for synthesizing a γ-nitrocarbonyl compound and for synthesizing a γ-dicarbonyl compound from a γ-nitrocarbonyl compound. For example, in one aspect of this invention, the initial effective concentration of the primary nitro compound in step a) is greater than about 1 molar, the molar ratio of the primary nitro compound to the α,β-unsaturated carbonyl compound is greater than about 1.05:1, and the molar ratio of the peroxide compound to the γ-nitrocarbonyl compound is in a range from about 1:1 to about 10:1. In another aspect, the initial effective concentration of the primary nitro compound in step a) is greater than about 1.3 molar, the molar ratio of the primary nitro compound to the α,β-unsaturated carbonyl compound is within a range from about 1.075:1 to about 1.15:1, and the molar ratio of the peroxide compound to the γ-nitrocarbonyl compound is in a range from about 1:1 to about 6:1.

According to another aspect of this invention, the process for producing a γ-dicarbonyl compound from an α,β-unsaturated carbonyl compound can further comprise a step of isolating the γ-dicarbonyl compound from the aqueous reaction mixture. As provided herein, the isolation step can include an extraction of the γ-dicarbonyl compound from the aqueous reaction mixture with an organic solvent. Suitable organic solvents, including halogenated organic solvents, also were provided herein.

In this process, as in the process for synthesizing a γ-nitrocarbonyl compound above, the γ-nitrocarbonyl compound can be produced by first forming a mixture of a base, a primary nitro compound, and water. Then, this mixture can be contacted with an α,β-unsaturated carbonyl compound to produce the γ-nitrocarbonyl compound, generally in yields of at least about 75 mole %. With or without isolation of the γ-nitrocarbonyl compound from the reaction mixture, a γ-dicarbonyl compound subsequently can be produced by contacting with a peroxide compound, at a molar ratio of the peroxide compound to the γ-nitrocarbonyl compound which falls within a range described herein (e.g., from about 1:1 to about 15:1).

Synthesizing Pyrrole Compounds

The present invention further provides a process for producing a pyrrole compound. Such a process can comprise (or alternatively, consist essentially of, or consist of) the following steps:

a) contacting a γ-nitrocarbonyl compound, a peroxide compound, a base, and water, wherein a molar ratio of the peroxide compound to the γ-nitrocarbonyl compound is in a range from about 1:1 to about 15:1;

b) forming a γ-dicarbonyl compound; and c) contacting the γ-dicarbonyl compound with ammonia or an ammonium salt to produce the pyrrole compound.

The first two steps of this process, step a) and step b), the synthesis of γ-dicarbonyl compounds from γ-nitrocarbonyl compounds, are discussed herein. Any embodiments for producing the γ-nitrocarbonyl compound and/or the γ-dicarbonyl compound described herein may be utilized in processes contemplated to produce the pyrrole compound and, accordingly, are encompassed by this invention.

For example, after step b) of this process, the γ-dicarbonyl compound can be isolated from the aqueous reaction mixture using, for example, an extraction procedure with an organic solvent (e.g., a halogenated organic solvent). Subsequently, the isolated γ-dicarbonyl compound can be contacted with ammonia or an ammonium salt to produce the pyrrole compound. Alternatively, step a) through step c) of the process can be conducted in a single reactor. That is, this process can be a one-pot synthesis of a pyrrole compound from a γ-nitrocarbonyl compound.

Step c) of this process produces a pyrrole compound by contacting a γ-dicarbonyl compound with ammonia or an ammonium salt. This step of the process can be conducted in accordance with the general procedure for producing 2,5-dimethylpyrrole from 2,5-hexanedione described in Young et al., *Org. Syn. Coll.*, Vol. 2 (1943), p. 219, the disclosure of which is incorporated herein by reference in its entirety. Non-limiting examples of suitable ammonium salts that can be employed in this process include ammonium carbonate, ammonium acetate, and the like, or a combination thereof.

According to one aspect of this invention, the γ-nitrocarbonyl compound has the formula:

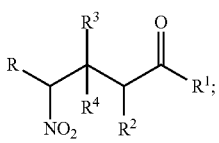

(III)

the γ-dicarbonyl compound has the formula:

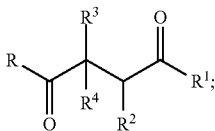

(IV)

and the pyrrole compound has the formula:

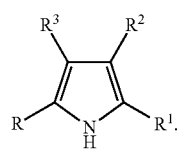

(V)

As noted above, these formulas are not designed to show stereochemistry or isomeric positioning of the different moieties (e.g., these formulas are not intended to show cis or trans isomers), although such compounds are contemplated and encompassed by these formulas. R, $R^1$, $R^2$, and $R^3$ have been described herein and can be utilized to describe aspects of the method for synthesizing a pyrrole compound having formula (V) utilizing the γ-nitrocarbonyl compound having formula (III) and the γ-dicarbonyl compound having formula (IV). In the process for producing a pyrrole compound having formula (V), $R^4$ is a hydrogen atom in formulas (II), (III) and (IV).

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The methyl vinyl ketone (3-buten-2-one, 99%) used in the Examples was purchased from Aldrich and distilled under nitrogen before use. All other materials were used as received, as listed in Table I below.

TABLE I

Materials used in the Examples.

| Material | Source | Purity (%) | MW | Comments |
|---|---|---|---|---|
| Potassium Carbonate | Aldrich | 99.7 | 138.2 | Anhydrous, reagent grade |
| $H_2O$ | In house | | 18 | Distilled water |
| Nitroethane | Aldrich | 96 | 75.1 | Boiling Point: 112-116° C.; Density: 1.045 g/cc |
| 2,5-Hexanedione | Aldrich | 99 | 70.1 | Boiling Point: 37° C. at 145 mmHg and 81° C. at 760 mmHg; density: 0.885 g/cc |
| Hydrogen Peroxide | Aldrich | 30% in water | 34 | Cold Stored |
| Dichloromethane | Aldrich | 99 | 84.9 | Boiling Point: 40° C.; density: 1.325 g/cc |
| Ammonium Carbonate | Aldrich | 99 | 78.1 | Cold stored |
| Ethyl Alcohol | Aldrich | 99 | 46.1 | Anhydrous |

Gas Chromatograph (GC) analyses were conducted on an Agilent 6890 GC System, using a HP-PONA column (methyl siloxane, capillary 50 m×200 μm×0.5 μm nominal), with temperature ramping at a rate of 10° C./min from 30° C. to 250° C. Standards for methyl vinyl ketone, 2,5-dimethylpyrrole, and other materials were used to identify the reactants and products, and to monitor the course of the reactions.

Comparative Example 1

Synthesis of 2,5-Hexanedione using the 2-Step Process Described in Ballini

Comparative Example 1 employed substantially the same procedure described in Ballini et al., J. Org. Chem., 2003, 68, 9173-9176, the disclosure of which is incorporated herein by reference in its entirety. The first step is a condensation reaction, and the second step is an oxidation reaction.

To a four-neck flask equipped with a magnetic stirrer, thermometer, condenser and circulating nitrogen, potassium carbonate (4.15 g, 30 mmol) and water (20 ml) were charged under a nitrogen blanket. A clear solution was obtained in about 10 minutes. To the reactor, nitroethane (1.29 g or 1.23 mL, 16.5 mmol) was charged. Note that a 10% excess of nitroethane was used. The mixture was stirred for 10 minutes, followed by charging methyl vinyl ketone (1.06 g or 1.24 mL, 15 mmol) into the reactor. The reaction continued for three hours at room temperature, at which time hydrogen peroxide (30%, 40 ml, 353 mmol) was added to the reactor. The reaction continued at room temperature for 16 hours. Note that in Ballini, the reaction was left overnight, which we have interpreted to be a time period of approximately 16 hours. The conversions from both steps of the reaction, nitro-substitution (condensation) and formation of 2,5-hexanedione (oxidation), were monitored by GC analysis.

The overall yield to 2,5-hexanedione in Comparative Example 1 was 64%, based on the limiting reactant (methyl vinyl ketone).

Example 2

Synthesis of a γ-Nitrocarbonyl (5-Nitro-2-Hexanone) with an Improved Condensation Step The impact of reaction time in the condensation step was evaluated in Example 2, which is illustrated by the following reaction scheme:

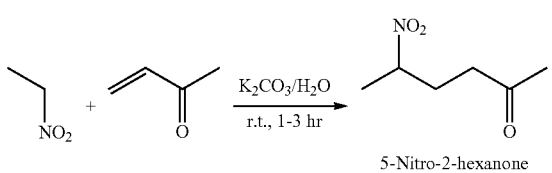

5-Nitro-2-hexanone

The condensation reaction was conducted in accordance with the following procedure. To a four-neck flask equipped with a magnetic stirrer, thermometer, condenser and circulating nitrogen, potassium carbonate (4.15 g, 30 mmol) and water (20 ml) were charged under nitrogen blanket. A clear solution was obtained in about 10 minutes. To the reactor, nitroethane (1.29 g or 1.23 mL, 16.5 mmol) was charged. The mixture was stirred for 10 minutes, followed by charging methyl vinyl ketone (1.06 g or 1.24 mL, 15 mmol) into the reactor. The reaction was allowed to continue for 3 hours at room temperature, but the conversion at several time intervals was determined by sampling a small aliquot at the respective time interval.

FIG. 1 compares the GC plots of the samples taken from the condensation reaction mixture at reaction times of 30 minutes, 1 hour, and 2 hours. Unexpectedly, longer reaction times favored the formation of impurities and other by-products at the expense of the desired 5-nitro-2-hexanone product.

Table II lists the GC area percents of the methyl vinyl ketone and nitroethane reactants, the 5-nitro-2-hexanone product, and reaction impurities at the respective reaction times of 30 minutes, 1 hour, and 2 hours.

TABLE II

Condensation Reaction Purity as a Function of Reaction Time.

| Reaction Time | methyl vinyl ketone | nitro-ethane | 5-nitro-2-hexanone | Impurity 1 | Impurity 2 | Impurity 3 |
|---|---|---|---|---|---|---|
| 30 min | 0.35 | 0.93 | 92.46 | 0.68 | 1.96 | 3.62 |
| 1 hour | 0.60 | 1.58 | 87.49 | 0.93 | 3.30 | 6.10 |
| 2 hours | 2.34 | 15.26 | 34.09 | 4.20 | 22.69 | 21.42 |

Example 3

Synthesis of a γ-Dicarbonyl (2,5-Hexanedione) using an Improved Oxidation Step

The impact of reaction temperature and time in the oxidation step was evaluated in Example 3, which is illustrated by the following reaction scheme:

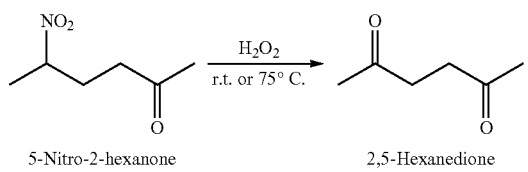

5-Nitro-2-hexanone      2,5-Hexanedione

The first step (i.e., the condensation reaction) of Example 3 was conducted in the same manner as that of Example 2, except that the reaction was allowed to continue for only 1 hour. Then, hydrogen peroxide (30%, 40 mL, 353 mmol) was added to the reactor, followed by increasing the reaction temperature to 75° C., which was maintained for two hours. The conversions from both steps of the reaction were monitored by GC analysis.

Figure 2:
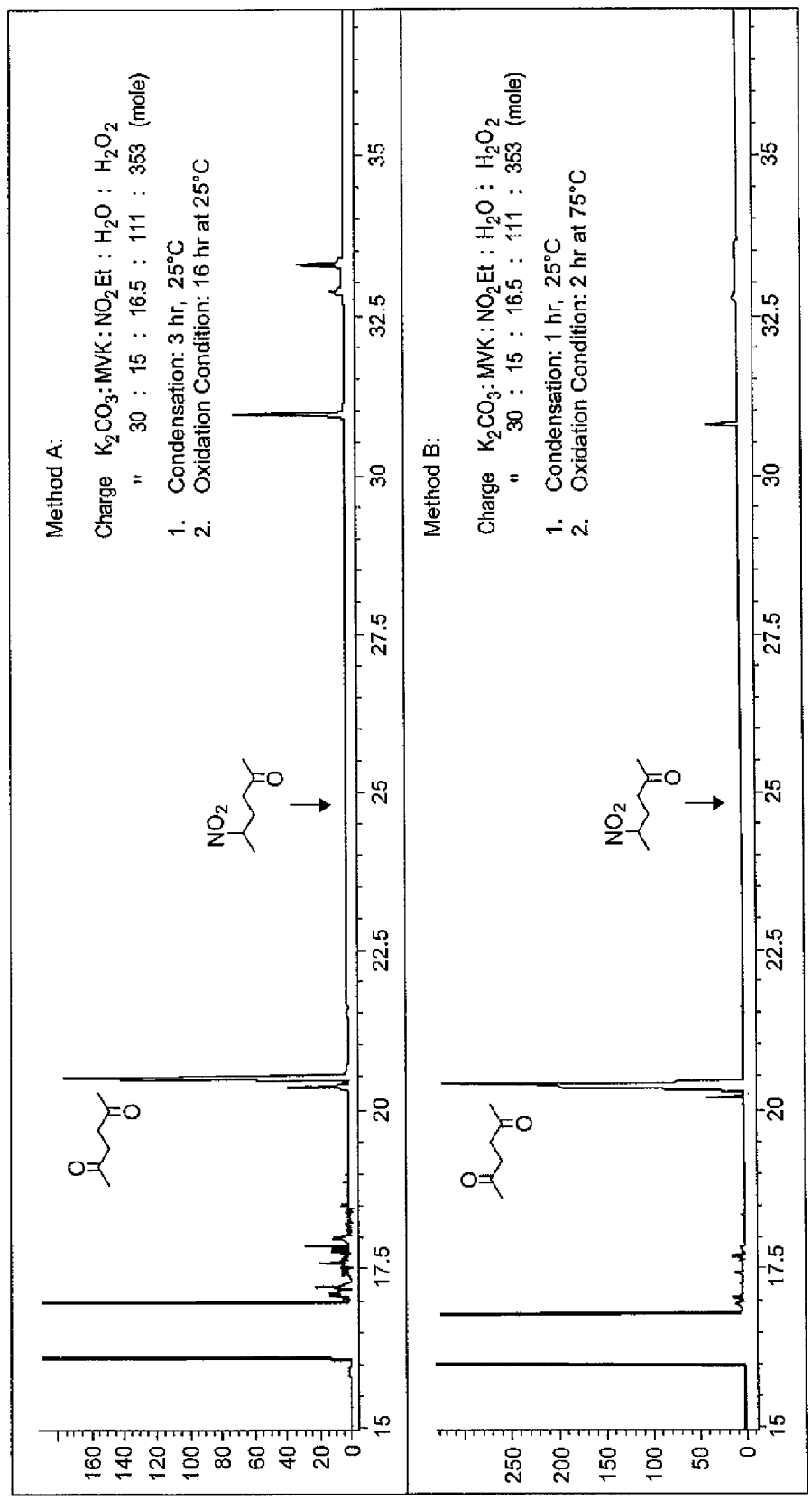
FIG. 2 presents Gas Chromatograph plots of the reaction mixtures of Example 3 (Method B) and Comparative Example 1 (Method A).

In FIG. 2, the synthesis procedure of Comparative Example 1 is listed as Method A, while the synthesis procedure of Example 3 is listed as Method B. MVK is used an abbreviation for methyl vinyl ketone, NO₂Et for nitroethane, and molar quantities are in mmol. FIG. 2 compares the GC plots of samples taken after both the condensation and oxidation steps to produce 2,5-hexanedione. The oxidation step of the method of Example 3 (Method B) was conducted at 75° C. but, interestingly, the higher reaction temperature did not lead to more impurities or by-products, and the complete conversion of the 5-nitro-2-hexanone intermediate to 2,5-hexanedione was accomplished in only 2 hours.

Example 4

Synthesis of a γ-Dicarbonyl (2,5-Hexanedione) using Reduced Quantities of Water and Hydrogen Peroxide The impact of reducing the amount of water present in the reaction mixture and reducing the molar ratio of the peroxide compound (hydrogen peroxide) to the γ-nitrocarbonyl compound (5-nitro-2-hexanone) was evaluated in Example 4.

Example 4 was conducted in accordance with the following procedure. To a four-neck flask equipped with a magnetic stirrer, thermometer, condenser and circulating nitrogen, potassium carbonate (4.15 g, 30 mmol) and water (10 mL) were charged under nitrogen blanket. A clear solution was obtained in about 10 minutes. To the reactor, nitroethane (1.29 g or 1.23 mL, 16.5 mmol) was charged. The mixture was stirred for 10 minutes, followed by charging methyl vinyl ketone (1.06 g or 1.24 mL, 15 mmol) into the reactor. The reaction continued for one hour at room temperature, followed by the addition of hydrogen peroxide (30%, 10 mL, 88.3 mmol) to the reactor. The reaction temperature was increased to 75° C., and maintained at that temperature for two hours. The conversions from both steps of the reaction were monitored by GC analysis.

Figure 3:
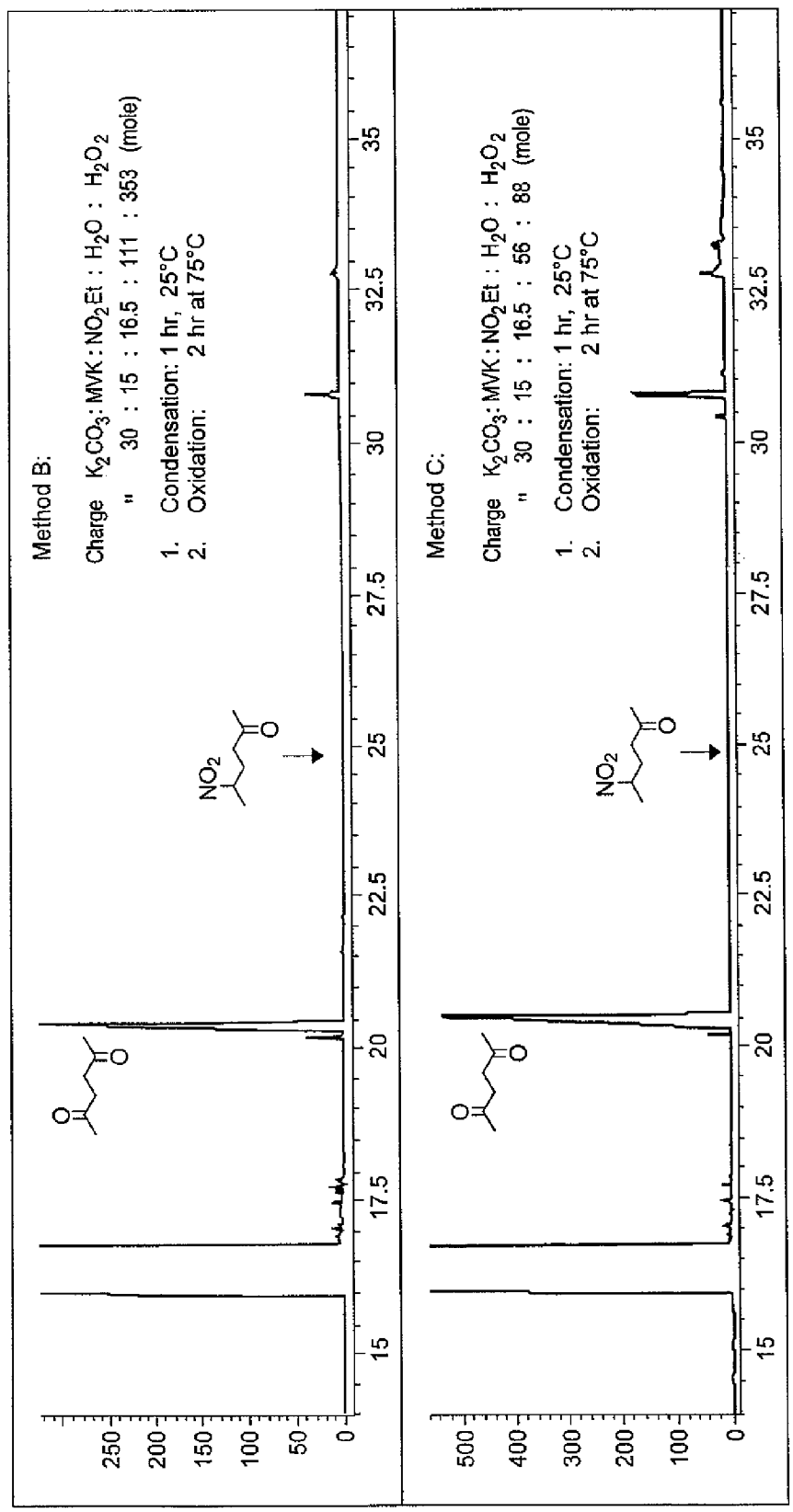
FIG. 3 presents Gas Chromatograph plots of the reaction mixtures of Example 3 (Method B) and Example 4 (Method C).

In FIG. 3, the synthesis procedure of Example 3 is listed as Method B, while the synthesis procedure of Example 4 is listed as Method C. MVK is used an abbreviation for methyl vinyl ketone, NO₂Et for nitroethane, and molar quantities are in mmol. FIG. 3 compares the GC plots of samples taken after both the condensation and oxidation steps to produce 2,5-hexanedione. The GC area yield in Example 4 was 87 percent and the isolated yield was 71 percent. Example 4 employed one-half of the water and one-quarter of the hydrogen peroxide used in Example 3, yet did not significantly impact the overall yield of 2,5-hexanedione.

Example 5

Synthesis of a γ-Dicarbonyl (2,5-Hexanedione) using Reduced Quantities of Water and Hydrogen Peroxide The impact of reducing the amount of water present in the reaction mixture and reducing the molar ratio of the peroxide compound (hydrogen peroxide) to the γ-nitrocarbonyl compound (5-nitro-2-hexanone) was evaluated in Example 5.

Example 5 was conducted in accordance with the following procedure. To a four-neck flask equipped with a magnetic stirrer, thermometer, condenser and circulating nitrogen, potassium carbonate (41.5 g, 300 mmol) and water (100 mL) were charged under nitrogen blanket. A clear solution was obtained in about 10 minutes. To the reactor, nitroethane (12.9 g or 12.3 mL, 165 mmol) was charged. The mixture was stirred for 10 minutes, followed by charging methyl vinyl ketone (10.6 g or 12.4 mL, 150 mmol) to the reactor. The reaction continued for one hour at room temperature, followed by the addition of hydrogen peroxide (30%, 25 mL, 220 mmol) to the reactor. After the addition of hydrogen peroxide, an exotherm increased the reaction temperature to 90° C. within one hour. Using GC analysis, it was determined that the reaction was complete within the one hour time period.

Figure 4:
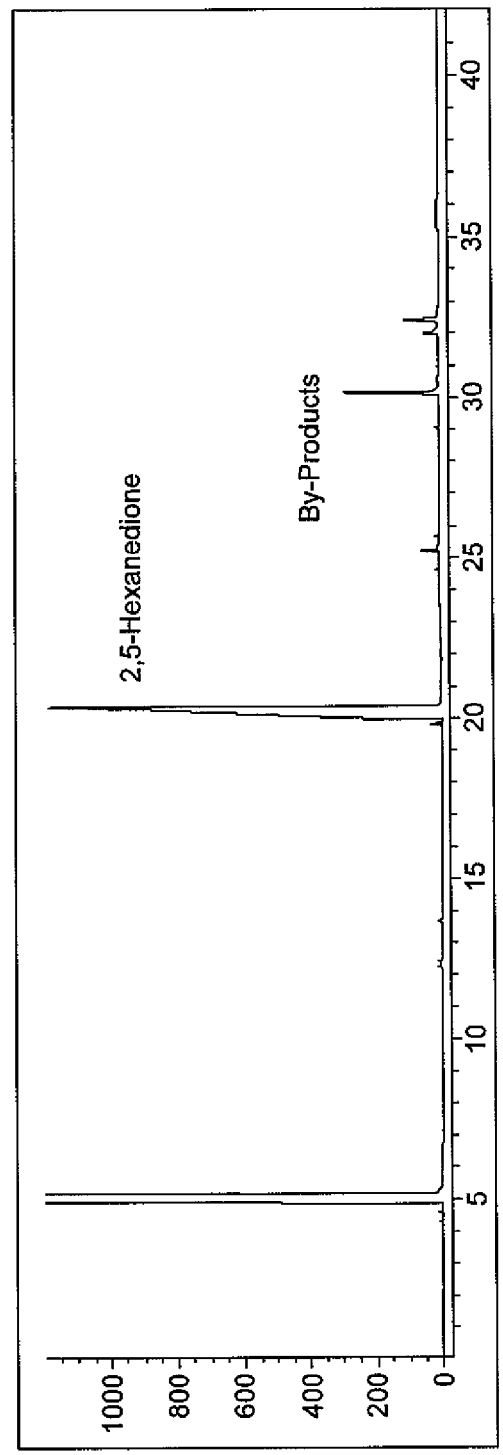
FIG. 4 presents a Gas Chromatograph plot of the reaction mixture of Example 5.

FIG. 4 is a GC plot of a sample taken from the final reaction mixture after both the condensation and oxidation steps to produce 2,5-hexanedione in accordance with Example 5. Example 5 employed one-half of the water and one-sixteenth of the hydrogen peroxide used in Comparative Example 1, and was conducted in about 2 hours, and yet resulted in much higher yield than in Comparative Example 1. The overall yield to 2,5-hexanedione in Example 5 was 86%, based on the limiting reactant (methyl vinyl ketone).

Example 6

Isolation and Purification of a γ-Dicarbonyl (2,5-Hexanedione)

The procedure employed by Ballini described a gel chromatography method for isolating and purifying the diketone product from the reaction mixture. Example 6 employed a solvent extraction of the aqueous reaction mixture of Example 5, which was conducted in accordance with the following procedure. The aqueous reaction mixture was extracted with 200 mL of dichloromethane in a separation funnel. The bottom organic layer was dried over anhydrous magnesium sulfate overnight (approximately 16 hours). The solvent was removed using a rotary evaporator. The crude 2,5-hexanedione product appeared as light yellow oil. This product was further purified by vacuum distillation, resulting in the final product as a colorless liquid. Product identity was confirmed by comparison to a known reference standard using GC analysis. The 2,5-hexanedione product was very soluble in water.

Ethyl acetate and toluene also were tested as potential extraction solvents, but dichloromethane was determined to be the most suitable for both high efficiency and inertness. Dichloromethane was more efficient than aromatic solvents, such as toluene. Ethyl acetate, a structurally promising solvent, was found to create by-products, or multiple components in the organic phase, during the extraction.

Table III lists the uptake of the desired product (2,5-hexanedione) from the reaction mixture by dichloromethane, determined by area percentage using GC analysis.

TABLE III

Uptake of 2,5-hexanedione in dichloromethane.

| Extraction | Dichloromethane (mL) | Product Uptake (%) |
|---|---|---|
| 1 | 100 | 94.8 |
| 2 | 100 | 4.6 |
| 3 | 100 | 0.4 |
| 4 | 100 | 0.1 |
| 5 | 100 | 0.1 |

Example 7

Synthesis of a γ-Dicarbonyl (2,5-Hexanedione) using Reduced Quantities of Water and Hydrogen Peroxide, and Subsequent Isolation and Purification The impact of reducing the amount of water present in the reaction mixture and reducing the molar ratio of the peroxide compound (hydrogen peroxide) to the γ-nitrocarbonyl compound (5-nitro-2-hexanone) was evaluated in Example 7.

Example 7 was conducted in accordance with the following procedure. To a four-neck flask equipped with a magnetic stirrer, thermometer, condenser and circulating nitrogen, potassium carbonate (41.5 g, 300 mmol) and water (100 mL) were charged under nitrogen blanket. A clear solution was obtained in about 10 minutes. To the reactor, nitroethane (12.9 g or 12.3 mL, 165 mmol) was charged over the course of 1 minute, resulting in a temperature increase from 25° C. to 40° C. in 5 minutes. When the reactor temperature subsided to 25° C., methyl vinyl ketone (10.6 g or 12.4 mL, 150 mmol) was charged to the reactor over a 2-minute time interval. The reactor temperature increased from 25° C. to 46° C. within 5 minutes, then subsiding gradually to room temperature over the next 30 minutes. At 1 hour reaction time (from the addition of methyl vinyl ketone), hydrogen peroxide (30%, total 25 mL, 220 mmol) was added to the reactor in four portions. Each of the four portions was added slowly over a period of 10 minutes, and each addition of the hydrogen peroxide resulted in an exotherm. The intervals between the additions were such that the reactor temperature did not exceed 65° C. Reaction time was 1 hour from the first addition of the hydrogen peroxide.

The aqueous reaction mixture was extracted 3 times with 100 mL of dichloromethane in a separation funnel. The bottom organic layer was dried over anhydrous magnesium sulfate overnight (approximately 16 hours). The solvent was removed using a rotary evaporator. The crude 2,5-hexanedione product appeared as light yellow oil. This product was further purified by vacuum distillation, resulting in 12.2 g of the final product as a colorless liquid. The overall isolated yield of 2,5-hexanedione in Example 7 was 71%, based on the limiting reactant (methyl vinyl ketone). The purity, determined by GC analysis, was 97%.

Example 8

Synthesis of a Pyrrole Compound (2,5-Dimethylpyrrole) from a γ-Dicarbonyl Compound (2,5-Hexanedione)

Example 8 employed substantially the same procedure described in Young et al., *Org. Syn. Coll.*, Vol. 2 (1943), p. 219, the disclosure of which is incorporated herein by reference in its entirety. Example 8 was conducted in accordance with the following procedure. To a 50-mL three-neck flask equipped with an oil bath, a condenser, a magnetic stirrer, and a nitrogen inlet, 2,5-hexanedione (acetonylacetone, 10 g, 88 mmol) and ammonium carbonate (20 g, 175 mmol) were charged under nitrogen. While stirring the contents and under a slow nitrogen purge, the oil bath was maintained at 95° C. for 90 minutes, and then the bath temperature was raised to 115° C. and maintained at this temperature for one hour. The reaction mixture was extracted with dichloromethane and the organic layer was dried over anhydrous magnesium sulfate overnight in accordance with the procedure described in Example 6. The solvent was removed using a rotary evaporator, and the crude 2,5-dimethylpyrrole product was further purified by vacuum distillation. Air exposure was kept to a minimum.

Example 9

Synthesis of a Pyrrole Compound (2,5-Dimethylpyrrole) from a γ-Dicarbonyl Compound (2,5-Hexanedione)

Example 9 employed substantially the same procedure as Example 8, as follows. To a 100-mL three-neck flask equipped with a heating element, a condenser, a magnetic stirrer, and a nitrogen inlet, 2,5-hexanedione (20 g, 176 mmol) and ammonium carbonate (40 g, 350 mmol) were charged under nitrogen. While stirring the contents and under a slow nitrogen purge, the reaction temperature was increased to 95° C. over a period of 1 hour, and maintained at this temperature for 90 minutes. The reaction temperature then was raised to 115° C. over a period of 30 minutes, and maintained at this temperature for 30 minutes. The reaction mixture was cooled and the upper, organic layer removed. The lower layer was extracted with 10 mL of dichloromethane, added to the organic layer, and the organic layer was dried over anhydrous magnesium sulfate. The solvent was removed using a rotary evaporator, and the crude 2,5-dimethylpyrrole product was further purified by vacuum distillation. Approximately 13 grams were collected at about 60° C. and 10 mmHg. The yield of 2,5-dimethylpyrrole after isolation and purification was 78%. The purity, determined by GC analysis, was 99.4%.

We claim:

1. A process for producing a γ-dicarbonyl compound comprising:
   a) contacting a γ-nitrocarbonyl compound, a peroxide compound, a base, and water, wherein a molar ratio of the peroxide compound to the γ-nitrocarbonyl compound is in a range from about 1:1 to about 15:1; and
   b) forming the γ-dicarbonyl compound; wherein:
   the γ-nitrocarbonyl compound has the formula:

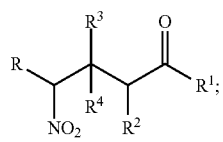

(III)

and
the γ-dicarbonyl compound has the formula:

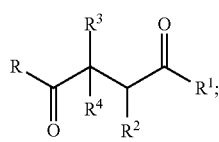

(IV)

wherein:
R, $R^1$, $R^2$, $R^3$, and $R^4$ independently are a hydrogen atom, a $C_1$-$C_{30}$ organyl group, a $C_1$-$C_{30}$ organyl group consisting of inert functional groups, or a $C_1$-$C_{30}$ hydrocarbyl group.

2. The process of claim 1, wherein the molar ratio of the peroxide compound to the γ-nitrocarbonyl compound is in a range from about 1:1 to about 10:1.

3. The process of claim 1, wherein step b) is conducted at a temperature in a range from about 40° C. to about 100° C.

4. The process of claim 1, wherein the contacting of the γ-nitrocarbonyl compound, the peroxide compound, the base, and water is initiated at a temperature in a range from about 20° C. to about 30° C., and an exotherm results in a temperature in a range from about 40° C. to about 100° C.

5. The process of claim 1, wherein the γ-dicarbonyl compound is produced in a yield of at least about 70 mole %.

6. The process of claim 1, wherein:
   the base is an alkali metal carbonate;
   the peroxide compound is hydrogen peroxide; or
   both.

7. The process of claim 6, wherein the alkali metal carbonate is potassium carbonate.

8. The process of claim 1, wherein R and $R^1$ independently are a $C_1$-$C_{18}$ hydrocarbyl group, and $R^2$, $R^3$, and $R^4$ are hydrogen.

9. The process of claim 8, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

10. The process of claim 1, further comprising isolating the γ-dicarbonyl compound, wherein the isolating comprises an extraction of the γ-dicarbonyl compound with an organic solvent.

11. A process for producing a pyrrole compound comprising:
    a) contacting a γ-nitrocarbonyl compound, a peroxide compound, a base, and water, wherein a molar ratio of the peroxide compound to the γ-nitrocarbonyl compound is in a range from about 1:1 to about 15:1; and
    wherein the γ-nitrocarbonyl compound has the formula:

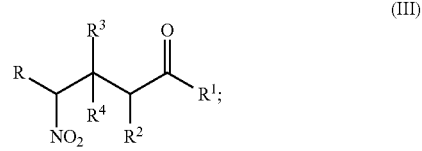

(III)

b) forming a γ-dicarbonyl compound having the formula:

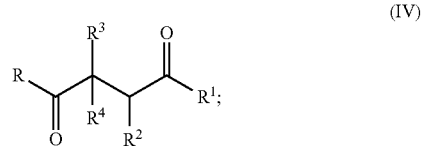

(IV)

and
c) contacting the γ-dicarbonyl compound with ammonia or an ammonium salt to produce the pyrrole compound; wherein:
the pyrrole compound has the formula:

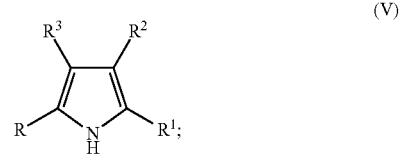

(V)

wherein:
$R^4$ is a hydrogen atom, and R, $R^1$, $R^2$, and $R^3$ independently are a hydrogen atom, a $C_1$-$C_{30}$ organyl group, a $C_1$-$C_{30}$ organyl group consisting of inert functional groups, or a $C_1$-$C_{30}$ hydrocarbyl group.

12. The process of claim 11, wherein the molar ratio of the peroxide compound to the γ-nitrocarbonyl compound is in a range from about 1:1 to about 10:1.

13. The process of claim 11, wherein step b) is conducted at a temperature in a range from about 40° C. to about 100° C.

14. The process of claim 11, wherein:
the base is an alkali metal carbonate;
the peroxide compound is hydrogen peroxide; or
both.

15. The process of claim 14, wherein the alkali metal carbonate is potassium carbonate.

16. The process of claim 11, wherein the ammonium salt is ammonium carbonate, ammonium acetate, or a combination thereof.

17. The process of claim 11, wherein R and $R^1$ independently are a $C_1$-$C_{18}$ hydrocarbyl group, and $R^2$ and $R^3$ are hydrogen.

18. The process of claim 17, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

19. The process of claim 11, further comprising isolating the γ-dicarbonyl compound before step c), wherein the isolating comprises an extraction of the γ-dicarbonyl compound with an organic solvent.

20. The process of claim 19, wherein the organic solvent is a $C_1$ to $C_{10}$ halogenated organic solvent.

21. A process for producing a pyrrole compound comprising:
a) contacting a primary nitro compound, an α,β-unsaturated carbonyl compound, a base, and water to produce a γ-nitrocarbonyl compound having the formula:

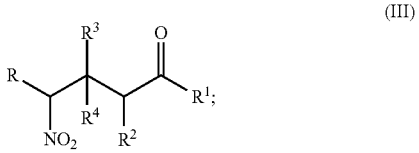
(III)

b) contacting a peroxide compound with the γ-nitrocarbonyl compound at a molar ratio of the peroxide compound to the γ-nitrocarbonyl compound in a range from about 1:1 to about 15:1 to produce a γ-dicarbonyl compound having the formula:

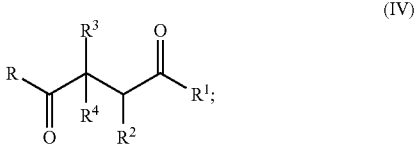
(IV)

and
c) contacting the γ-dicarbonyl compound with ammonia or an ammonium salt to produce the pyrrole compound;
wherein:
the pyrrole compound has the formula:

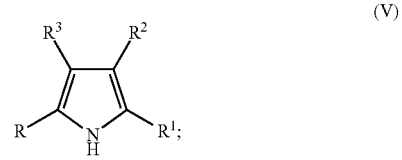
(V)

wherein:
$R^4$ is a hydrogen atom, and R, $R^1$, $R^2$, and $R^3$ independently are a hydrogen atom, a $C_1$-$C_{30}$ organyl group, a $C_1$-$C_{30}$ organyl group consisting of inert functional groups, or a $C_1$-$C_{30}$ hydrocarbyl group.

22. The process of claim 21, wherein the molar ratio of the peroxide compound to the γ-nitrocarbonyl compound is in a range from about 1:1 to about 10:1.

23. The process of claim 21, wherein steps a) and b) are conducted in a single reactor.

24. The process of claim 21, wherein step b) is conducted at a temperature in a range from about 40° C. to about 100° C.

25. The process of claim 21, wherein:
the γ-nitrocarbonyl compound is produced in a yield of at least about 75 mole %; and
the γ-dicarbonyl compound is produced in an overall yield of at least about 70 mole %.

26. The process of claim 21, wherein:
the base is an alkali metal carbonate;
the peroxide compound is hydrogen peroxide; or
both.

27. The process of claim 26, wherein the alkali metal carbonate is potassium carbonate.

28. The process of claim 21, wherein the ammonium salt is ammonium carbonate, ammonium acetate, or a combination thereof.

29. The process of claim 21, wherein R and $R^1$ independently are a $C_1$-$C_{18}$ hydrocarbyl group, and $R^2$ and $R^3$ are hydrogen.

30. The process of claim 29, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

31. The process of claim 21, further comprising isolating the γ-dicarbonyl compound before step c), wherein the isolating comprises an extraction of the γ-dicarbonyl compound with an organic solvent.

32. The process of claim 31, wherein the organic solvent is dichloromethane.

* * * * *

UNITED STATES PATENT AND TRADEMARK OFFICE
CERTIFICATE OF CORRECTION

| | | |
|---|---|---|
| PATENT NO. | : 8,729,277 B2 | Page 1 of 1 |
| APPLICATION NO. | : 13/406677 | |
| DATED | : May 20, 2014 | |
| INVENTOR(S) | : Hu Yang et al. | |

It is certified that error appears in the above-identified patent and that said Letters Patent is hereby corrected as shown below:

On the Title Page

Item (73) Assignee:

"Chevron Philips" should be changed to --Chevron Phillips--

Signed and Sealed this
Eighteenth Day of November, 2014

Michelle K. Lee
*Deputy Director of the United States Patent and Trademark Office*